United States Patent
Aben et al.

(10) Patent No.: US 11,911,203 B2
(45) Date of Patent: Feb. 27, 2024

(54) METHOD AND SYSTEM FOR REGISTERING INTRA-OBJECT DATA WITH EXTRA-OBJECT DATA

(71) Applicant: Pie Medical Imaging B.V., Maastricht (NL)

(72) Inventors: Jean-Paul Aben, Limbricht (NL); Chris Bouwman, Oirsbeek (NL); Bas Weijers, Maasmechelen (BE)

(73) Assignee: Pie Medical Imaging B.V., Maastricht (NL)

( * ) Notice: Subject to any disclaimer, the term of this patent is extended or adjusted under 35 U.S.C. 154(b) by 222 days.

(21) Appl. No.: 17/208,373

(22) Filed: Mar. 22, 2021

(65) Prior Publication Data
US 2021/0298708 A1     Sep. 30, 2021

(30) Foreign Application Priority Data
Mar. 26, 2020   (EP) .................................... 20165750

(51) Int. Cl.
*A61B 6/00* (2006.01)
*A61B 5/33* (2021.01)

(52) U.S. Cl.
CPC .............. *A61B 6/5235* (2013.01); *A61B 5/33* (2021.01); *A61B 6/481* (2013.01); *A61B 6/487* (2013.01); *A61B 6/504* (2013.01); *A61B 6/5217* (2013.01)

(58) Field of Classification Search
CPC ....... A61B 6/5235; A61B 5/318; A61B 6/481; A61B 6/487; A61B 6/504; A61B 8/12
See application file for complete search history.

(56) References Cited

U.S. PATENT DOCUMENTS

| 7,729,746 B2 | 6/2010 | Redel et al. |
| 7,930,014 B2 | 4/2011 | Huennekens et al. |

(Continued)

FOREIGN PATENT DOCUMENTS

| CN | 103800003 A | * | 5/2014 | |
| EP | 2873371 A1 | | 5/2015 | |
| WO | WO-9315658 A1 | * | 8/1993 | ............. A61B 6/481 |

OTHER PUBLICATIONS

Zhu, Hui, Kevin D. Oakeson, and Morton H. Friedman. "Retrieval of cardiac phase from IVUS sequences." Medical Imaging 2003: Ultrasonic Imaging and Signal Processing. vol. 5035. SPIE, 2003. (Year: 2003).*

(Continued)

*Primary Examiner* — Colin T. Sakamoto
*Assistant Examiner* — Tommy T Ly
(74) *Attorney, Agent, or Firm* — Gordon & Jacobson, P.C.

(57) ABSTRACT

Methods for correlating intraluminal data with x-ray image data involve providing x-ray image data of a tubular organ, providing intraluminal data of the tubular organ, synchronizing the x-ray image data with the intraluminal data based on a cardiac cycle extracted from an available input signal and/or the x-ray image data and/or the intraluminal data to match x-ray image data with intraluminal data in a specific cardiac phase, and co-registering x-ray image data with intraluminal data by creating a cumulative image at the specific cardiac phase which reconstructs the path followed by an intraluminal wire used for acquiring the intraluminal data to link the intraluminal data to spatial locations of the path followed by the wire within the x-ray image. A corresponding system and computer program are also disclosed. The method and systems can be controlled by one or more (Continued)

computer systems configured with specific executable instructions.

26 Claims, 28 Drawing Sheets

(56) References Cited

U.S. PATENT DOCUMENTS

| | | | |
|---|---|---|---|
| 8,565,859 B2 | 10/2013 | Wang et al. | |
| 9,811,939 B2 | 11/2017 | Aben et al. | |
| 2006/0058647 A1* | 3/2006 | Strommer | A61B 5/7475 600/434 |
| 2007/0123771 A1* | 5/2007 | Redel | A61B 6/466 600/407 |
| 2010/0094124 A1* | 4/2010 | Schoonenberg | A61B 8/5238 382/132 |
| 2012/0271162 A1* | 10/2012 | Liao | G06T 7/285 600/424 |
| 2013/0053664 A1* | 2/2013 | Jian | A61B 5/021 600/324 |
| 2014/0275995 A1 | 9/2014 | Sheehan | |
| 2015/0119705 A1* | 4/2015 | Tochterman | A61B 6/504 600/431 |
| 2015/0282890 A1* | 10/2015 | Cohen | A61B 5/1128 600/424 |
| 2019/0029624 A1* | 1/2019 | Kunio | A61B 6/00 |
| 2019/0175035 A1* | 6/2019 | Van Der Horst | A61B 5/0084 |
| 2020/0222018 A1 | 7/2020 | van Walsum et al. | |
| 2021/0085275 A1* | 3/2021 | Gopinath | A61B 6/541 |

OTHER PUBLICATIONS

"A novel dedicated 3-dimensional quantitative coronary analysis methodology for bifurcation lesions", Yoshinobu Onuma et al., EuroIntervention 2011; 6:1-00.

"A Real-Time Algorithm for Extraction of Heart Beat in Invasive Blood Pressure", Shalbaf et al., Biomed 2008, Proceedings 21, pp. 103-106.

"A Real-Time QRS Detection Algorithm", Pan et al., IEEE Transactions on Biomedical Engineering. BME-32 (3): 230-236.

"An overview of Medical Image registration Methods", Maintz et al., in symposium of the Belgian hospital physicists association: 1996.

"Automatic online layer separation for vessel enhancement in x-ray angiograms for percutaneous coronary interventions", Ma et al., Med Image Anal. Jul. 2017; 39:145-161.

"CAAS II: A Second Generation system for Off-Line and On-Line Quantitative Coronary Angiography", Groneschild E, et al., Cardiovascular Diagnosis 1994; 33: 61-75.

"Cardiac phase detection in intravascular ultrasound images", Matsumoto et al., SPIE Proceedings, Medical Imaging 2008: Ultrasonic Imaging and Signal Processing, vol. 6920, 69200D.

"Cascade Attention Machine for Occluded Landmark Detection in 2D X-Ray Angiography", Zhang et al., Jan. 2019 IEEE Winter Conference on Applications of Computer Vision (WACV).

"Coronary Artery Motion During the Cardiac Cycle and Optimal ECG triggering for Coronary imaging", Lu et al., Investigative Radiology 2001;36:250-256.

"Coronary Circulation", Berne R.B., Levy M.N. (2001), Cardiovascular Physiology, 8th Edition, Mosby/Elsevier, p. 227-240.

"Deep learning based guidewire segmentation in x-ray images", Wagner et al., SPIE Proceedings, Medical Imaging 2019: Physics of Medical Imaging, 1094844 (Mar. 1, 2019).

"Elastix: a toolbox for intensity-based medical image registration", Klein et al., Med. Imag. IEEE Trans. 29 (1), 196-205.

EP Search Report dated Oct. 13, 2020 of Application No. 20165750.9.

"Fast prospective detection of contrast inflow in x-ray angiograms with convolutional neural network and recurrent neural network", Ma et al., International Conference on Medical Image Computing and Computer-Assisted Intervention, Springer (2017) 453-461.

"Fully automatic and real-time catheter segmentation in x-ray fluoroscopy", Ambrosini et al., International Conference on Medical Image Computing and Computer-Assisted Intervention 2017, Springer. pp. 577-585.

"Layer separation for vessel enhancement in interventional x-ray angiograms using morphological filtering and robust PCA", Ma et al., Workshop on Augmented Environments for Computer-Assisted Interventions 2017, Springer. pp. 104-113.

"Measurement of Fractional Flow Reserve to Assess the Functional Severity of Coronary-Artery Stenoses," PIJLS et al., N Engl J Med 1996, 334:1703-1708.

"Multiscale Vessel Enhancement Filtering", Frangi et al., Medical Image Computing and Computer-Assisted Intervention—MICCAI 1998 Lecture Notes in Computer Science 1496/1998:130.

"On the inappropriateness of noninvasive multidetector computed tomography coronary angiography to trigger coronary revascularization: a comparison with invasive angiography", Sarno G et al., JACC Cardiovasc Interv. Jun. 2009;2(6):550-7.

"Skeletonization of gray-scale image from incomplete boundaries", Li et al., Proceedings of the International Conference on Image Processing, ICIP 2008, Oct. 12-15.

"Vessel Layer Separation in X-ray Angiograms with Fully Convolutional Network", Hao et al., Proc. SPIE 10576, Medical Imaging 2018: Image-Guided Procedures, Robotic Interventions, and Modeling.

* cited by examiner

2401

2402

2403

METHOD AND SYSTEM FOR REGISTERING INTRA-OBJECT DATA WITH EXTRA-OBJECT DATA

CROSS-REFERENCE TO RELATED APPLICATIONS

The present application claims priority from EP Appl. No. 20165750, filed on Mar. 26, 2020, entitled "METHOD AND SYSTEM FOR REGISTERING INTRA-OBJECT DATA WITH EXTRA-OBJECT DATA," herein incorporated by reference in its entirety.

BACKGROUND

1. Field

The present application relates to the technical field of medical imaging, particularly in percutaneous interventions, although it can find application in any field where there is the need to co-register intra-object imaging with extra-object imaging.

2. State of the Art

Coronary artery disease is the narrowing or blockage of the coronary arteries, usually caused by atherosclerosis. Atherosclerosis is the build-up of cholesterol and fatty deposits (called plaques) on the inner walls of the arteries. These plaques can restrict blood flow to the heart muscle by physically clogging the artery or by causing abnormal artery tone and function. Without an adequate blood supply, the heart becomes starved of oxygen and the vital nutrients it needs to work properly. This can cause chest pain called angina. If the blood supply to a portion of the heart muscle is cut off entirely, or if the energy demands of the heart become much greater than its blood supply, a heart attack (injury to the heart muscle) may occur or a stroke. Atherosclerosis is treated in arteries of the heart, head, neck, and peripheral portions of the body using many different methods. The most popular methods, such as angioplasty, bare metal stenting, drug eluting stenting (permanently implantable and biodegradable), various types of energy delivery and rotational atherectomy, all treat an artery equally around the circumference of a target length of the arterial lumen.

Presently, x-ray angiography is the imaging modality used during treatment of vascular diseases by means of a minimally invasive procedure also known as percutaneous coronary intervention (PCI). X-ray angiographic imaging is used to guide the intervention procedure to treat atherosclerosis. During PCI, a (interventional) cardiologist feeds a deflated balloon or other device on a catheter from the inguinal femoral artery or radial artery up through blood vessels until they reach the site of blockage in the artery. PCI usually involves inflating a balloon to open the artery with the aim to restore unimpeded blood flow. Stents or scaffolds may be placed at the site of the blockage to hold the artery open.

X-ray angiography is also a standard imaging technique for anatomical assessment of the coronary arteries and the diagnosis of vascular disease, known as x-ray diagnostics angiography. Even when the geometric dimensions of a stenosis are quantified by means of two-dimensional (2D) quantitative coronary analysis tools (QCA), as for instance taught by Gronenschild E, et al. in "*CAAS II: A Second Generation system for Off-Line and On-Line Quantitative Coronary Angiography*", Cardiovascular Diagnosis 1994; 33: 61-75, or by means of three-dimensional (3D) QCA, for instance as thought by Yoshinobu Onuma et al. in "*A novel dedicated 3-dimensional quantitative coronary analysis methodology for bifurcation lesions*", EuroIntervention 2011; 6:1-00, the translation of anatomic lumen reduction to hemodynamic stenosis severity is not straightforward since functional coronary lesion severity depends on coronary hemodynamics. This poor relation between anatomical and functional severity of coronary stenosis was also shown using new and promising non-invasive techniques using multidetector computed tomography coronary angiography (CCTA) by Sarno G et al. in "*On the inappropriateness of noninvasive multidetector computed tomography coronary angiography to trigger coronary revascularization: a comparison with invasive angiography*", JACC Cardiovasc Interv. 2009 June; 2(6):550-7. For intermediate coronary lesions, defined as luminal reduction of 30-70% for instance, it is not always obvious if the stenosis is a risk for the patient and if it is desired to take action. Overestimation of the severity of the stenosis can cause a treatment which in hindsight would not have been necessary. Therefore exposing the patient to risks that are not necessary. Underestimation of the stenosis, however, could induce risks because the patient is left untreated when the stenosis is in reality severe. Especially for these situations it is desired to have an additional functional assessment to aid in a good decision making.

Therefore, additional vascular imaging modalities are commonly performed during PCI to obtain additional information of the diseased vessel. For example atherosclerotic plaque, is assessed by intravascular imaging modalities, such as intravascular ultrasound (IVUS) or optical coherence tomography (OCT), during the intervention procedure. Another example of an additional imaging modality is intravascular fractional flow reserve, used to identify the hemodynamic significance of lesion. Fractional Flow Reserve (FFR) has been used increasingly over the last 15-20 years as a method to identify and effectively target the coronary lesion most likely to benefit from PCI. FFR is a technique used to measure pressure differences across a coronary artery stenosis to determine the likelihood that the stenosis impedes oxygen delivery to the heart muscle. The technique involves percutaneously inserting a pressure-transducing wire inside the coronary artery guided by x-ray coronary angiography and measuring the pressure behind (distal to) and before (proximal to) the lesion. This is best done in a hyperemic state because in the case of maximum hyperemia, blood flow to the myocardium is proportional to the myocardium perfusion pressure. FFR therefore provides a quantitative assessment of the functional severity of the coronary lesion as described by Pijls et al. in "*Measurement of Fractional Flow Reserve to Assess the Functional Severity of Coronary Artery Stenoses*," N Engl J Med 1996, 334:1703-1708. Due to the invasive nature of measure FFR with a pressure-transducing wire, this technique is also called invasive FFR. Another example of an intravascular imaging device to assess the hemodynamic significance of lesion is instantaneous wave-free ratio (iFR), which is similar to FFR with the exception that the imaging is performed at rest and no hyperemic state is required. Coronary Flow Reserve (CFR) is another example of intravascular imaging to assess the hemodynamic significance of lesion, which is defined as maximum increase in blood flow through the coronary arteries above the normal resting volume.

Intravascular imaging, such as IVUS, OCT, FFR, iFR, CFR, is performed during pullback of an intravascular device through a vessel and produces a stack of images showing vessel cross sections in case of IVUS or OCT. In case of FFR, iFR or CFR the resulting measurement is a pressure value. In general there are two approaches for intravascular imaging; a) an automatic pullback, in which the pullback of the intravascular imaging device is performed automatically with a predefined pullback speed, and b) a manual pullback, in which the (interventional) cardiologists pulls back the intravascular imaging device by hand.

The challenge with these imaging modalities it to correlate the position of a particular image, or measured value, with respect to its location in the vessel within an angiographic view. In practice the physician looks for anatomical landmarks, for example bifurcations or a number of side branches that can be recognized both on x-ray angiography and on the intravascular images in order to correlate the information of both imaging modalities with each other. However, this is time-consuming and prone to errors which might lead to not optimal treatment of vessel diseases. Furthermore, in case the intravascular imaging device results in a measured value, such as FFR, iFR or CFR, such correlation approach becomes even more difficult or even not possible.

A solution to this problem is disclosed in U.S. Pat. No. 7,729,746 in which the co-registration of intravascular images with x-ray angiography is performed by generation of a 3D reconstruction of the vessel based on two x-ray angiographic projections. In order to perform the co-registration, two additional x-ray fluoroscopic images are required in which the user identifies in each fluoroscopic image the tip of the intravascular transducer. This results in a 3D point in space which is used to perform the co-registration. This approach assumes that the center of the 3D model corresponds with the intravascular path in the vessel during pullback. Furthermore, any errors in the 2D segmentation of the vessel within the x-ray angiographic images will negatively influence the co-registration since they directly affect the 3D reconstruction of the vessel and its resulting centerline. These shortcomings were resolved in U.S. Pat. No. 9,811,939, in which the 3D model, consisting of only a 3D centerline representing the pullback path of the intravascular device, truly represents the intravascular path and the method does not rely on 2D segmentation of the vessel to generate the 3D model, however the method requires that information on the pullback speed is available. A further disadvantage of above methods is that they rely on a 3D model, which requires two x-ray angiographic images.

In U.S. Pat. No. 7,930,014 a method is disclosed of co-registration of vascular image with x-ray images by tracing the intravascular transducer, which is located on the tip of the guide-wire, during controlled pullback on x-ray fluoroscopy. A disadvantage of this method is that an automatic pullback of the intravascular wire is required.

In U.S. Pat. No. 8,565,859 a method is disclosed of co-registration of IVUS with x-ray images by tracing the IVUS transducer, which is located on the tip of the IVUS wire, during pullback on x-ray fluoroscopy. A disadvantage of this method is the restriction to IVUS and the limited accuracy of length assessment due to foreshortening or out-of-plane magnification errors, which is important when choosing the correct stent- and/or balloon-length during treatment of the vascular disease.

Thus, there is a need to improve the co-registration process of intravascular imaging modality (intra-object imaging) with x-ray angiographic imaging modality (inter-object imaging) to, at least partially, overcome the above drawbacks.

SUMMARY

It is thus an object of embodiments herein to provide improved methods and systems to register multimodality information including intraluminal data.

In accordance with embodiments herein, devices, computer program products and computer implemented methods are provided for correlating intraluminal data with x-ray image data, the devices, program products and methods comprising, under control of one or more computer systems configured with specific executable instructions:

providing x-ray image data of a tubular organ;
providing intraluminal data of the tubular organ;
synchronizing the x-ray image data with the intraluminal data based on a cardiac cycle extracted from an available input signal and/or the x-ray image data and/or the intraluminal data to match x-ray image data with intraluminal data in a specific cardiac phase; and
co-registering x-ray image data with intraluminal data by creating a cumulative image at the specific cardiac phase which reconstructs the path followed by an intraluminal wire used for acquiring the intraluminal data to link the intraluminal data to spatial locations of the path followed by the wire within the x-ray image.

According to an embodiment, the cumulative image can be created by extracting image frames from the x-ray image data containing the intraluminal wire at the same specific cardiac phase, and cumulating the image frames as extracted. Before forming the cumulative image, the intraluminal wire may be identified or segmented in the image frames.

The start of acquisition of the intravascular data can be optionally determined by analyzing the movement curve created by computing the absolute distance of the detected intraluminal wire between a reference frame and the remaining image frames of the sequence.

The x-ray image data typically comprise fluoroscopic image data obtained without contrast agent and angiography image data obtained with contrast agent. This is common in an acquisition session. The cumulative image is advantageously created from the fluoroscopic image data as there is no need to detect the vascular tree but just the wire path. The cumulative image so created can be, for example, superimposed on the angiography image data.

The radiopaque wire section extracted from the x-ray fluoroscopic image data may be advantageously used to compute the foreshortening along the length of a co-registered segment of the tubular organ and/or to translate pixels into millimeters.

If the intraluminal data comprises numeric values like pressures, such numeric values can be advantageously superimposed on the angiography image data at corresponding spatial locations and/or represented as a graph along the length of a co-registered segment of the tubular organ. Such representation may be, for example, help to determine if a lesion is focal or diffuse.

If the intraluminal data comprises intraluminal images, an embodiment comprises receiving an input to select a spatial location within the angiography image data and showing intraluminal images which has been taken from such spatial location.

Motion not due to cardiac cycle, like, for example, breathing and/or patient motion can be advantageously corrected to improve the registration process, for example by tracking the catheter tip within the x-ray fluoroscopic image data.

In an advantageous embodiment, the tracking is performed using a deep learning based Bayesian filtering approach.

If the x-ray image data and the intraluminal data have a known temporal relation, synchronizing the x-ray image data with the intraluminal data may comprise extracting a cardiac cycle from an ECG signal, the x-ray image data or the intraluminal data, selecting a specific cardiac phase, calculating delays between the specific cardiac phase and the x-ray image data and the intraluminal data, aligning the x-ray image data and the intraluminal data by correcting the delays as calculated.

If the x-ray image data and the intraluminal data have an unknown temporal relation, the method may further comprise extracting cardiac cycles from the x-ray image data, or from an ECG signal correlated with the x-ray image data, and from the intraluminal data, identifying a specific cardiac phase in the cardiac cycles as extracted, calculating delays between the specific cardiac phase, the x-ray image data and the intraluminal data, aligning the x-ray image data and the intraluminal data by correcting the delays as calculated.

In an embodiment, the reliability of an ECG signal is assessed by aligning the ECG signal with a template and determining a correlation function between the ECG signal and such template.

If the x-ray image data comprise image frames including a fixed element subject to cardiac motion like, for example, a catheter tip, an embodiment comprises determining the motion of the fixed element, for example through image segmentation techniques or machine learning, and extracting from such motion a cardiac cycle. The motion of the fixed element may advantageously comprise enhancing structures subject to cardiac motion in the image frames, for example by using techniques of principal component analysis.

If the intraluminal data comprises bi-dimensional images, an embodiment comprises determining the motion of the lumen border with respect to a reference point or line, like, for example, the location of the imaging probe used for acquiring the images and extracting from such motion a cardiac cycle. The motion of the lumen border may comprise calculating the distance from the reference point or line to the lumen border in each or part of the images and combining the distances as calculated to reconstruct a cardiac cycle.

If the intraluminal data comprises non-imaging data, such as pressure data, embodiments comprise determining periodic features in the non-imaging data and extracting from such periodic features a cardiac cycle.

Embodiments also relate to systems for registering x-ray images with intraluminal data of a tubular organ, which include an angiographic imaging apparatus for obtaining x-ray images of the tubular organ as well as an intravascular apparatus for obtaining intraluminal data of the tubular organ. The system can also include a combination device comprising a data processing module, and interface elements for receiving x-ray images from the angiographic imaging apparatus and intraluminal data from the intravascular apparatus. The data processing module can be configured to synchronize the x-ray image data with the intraluminal data based on a cardiac cycle extracted from an available input signal and/or the x-ray image data and/or the intraluminal data to match x-ray image data with intraluminal data in a specific cardiac phase and co-register the x-ray image data with intraluminal data by creating a cumulative image at the specific cardiac phase which reconstructs the path followed by an intraluminal wire used for acquiring the intraluminal data to link the intraluminal data to spatial locations of the path followed by the wire within the x-ray image performing one or more steps disclosed above.

In an embodiment, the combination device can be part of the angiography imaging apparatus. In this case, the data processing module of the combination device can be one of the processors of the angiographic imaging apparatus having access to the x-ray images and the angiographic imaging apparatus has an input for receiving intraluminal data from the intravascular apparatus.

The combination device may also be part of the intravascular apparatus. In this case, the data processing module of the combination device can be one of the processors of the intravascular apparatus having access to the intraluminal data and the intravascular apparatus has an input for receiving x-ray images from the x-ray imaging apparatus.

In an embodiment, the system can further comprise an ECG module interfaced with the x-ray apparatus, the intravascular apparatus, or the combination device to allow the data processing module to elaborate an ECG signal.

The x-ray images, the intravascular data, the ECG signal may be input to the combination device, at least partially, through a frame grabber, an A/D converter, a DICOM (Digital Imaging and Communications in Medicine) transfer protocol or combination thereof.

In an embodiment, the intravascular apparatus comprises an intraluminal wire having on the tip a sensor for collecting intraluminal data through a console while the intraluminal wire is pulled through a tubular organ, such sensor being suitable for collecting intraluminal data, like, for example, pressures or images, selected from the group consisting of: FFR, iFR, CFR, IVUS, OCT data.

BRIEF DESCRIPTION OF THE DRAWINGS

The characteristics of the invention and the advantages derived therefrom will be more apparent from the following description of non-limiting embodiments, illustrated in the annexed drawings, in which.

DETAILED DESCRIPTION OF A PREFERRED EMBODIMENT

The present application relates to a method and system for co-registration of an intravascular modality (intra-object) with x-ray angiographic imaging modality (inter-object). Co-registration in current application refers to the alignment of intravascular data and x-ray angiographic images from the same subject to map intra-object information into inter-object space. The method will mainly be disclosed by using FFR as example of an intervascular modality, but the method is not limited to FFR as in intravascular modality as such the method is also applicable for IVUS, OCT, iFR, CFR and the like. The intravascular wire (see FIG. 4A, FIG. 4B and corresponding description), which is inserted into a vessel of interest, consists of intravascular imaging sensor. Typically, the intravascular wire has radiopaque material present around the top of the intravascular wire. This radiopaque material (or section) is within a predefined distance of the intravascular imaging sensor and is in general just a few millimeters. The radiopaqueness of the intravascular sensor may vary depending on the type of intravascular wire, which can also be dependent on the type of intravascular device.

Figure 7:
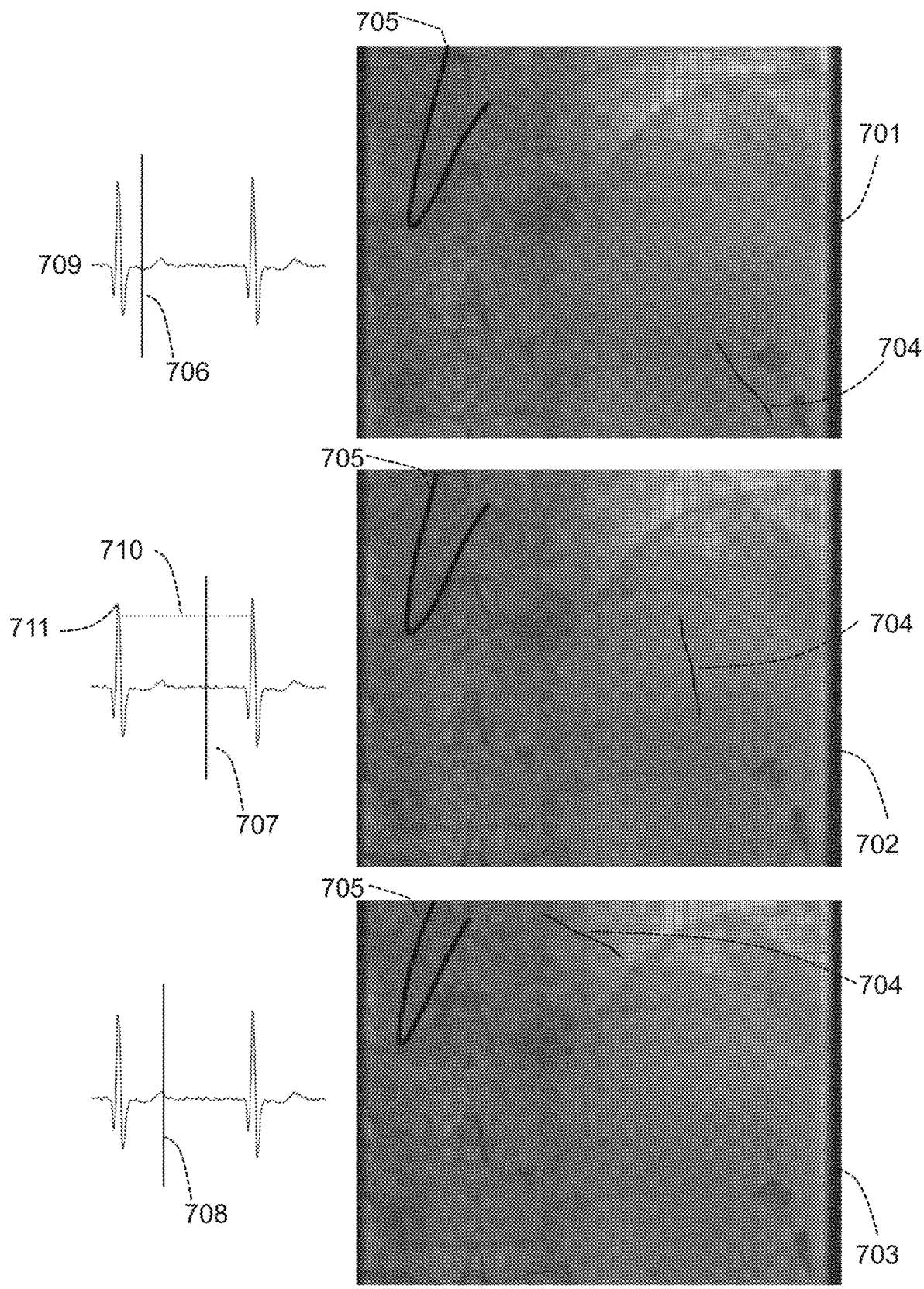
FIG. 7 illustrates the x-ray fluoroscopic image sequence which covers the pullback of the intravascular imaging device.
Figure 13:
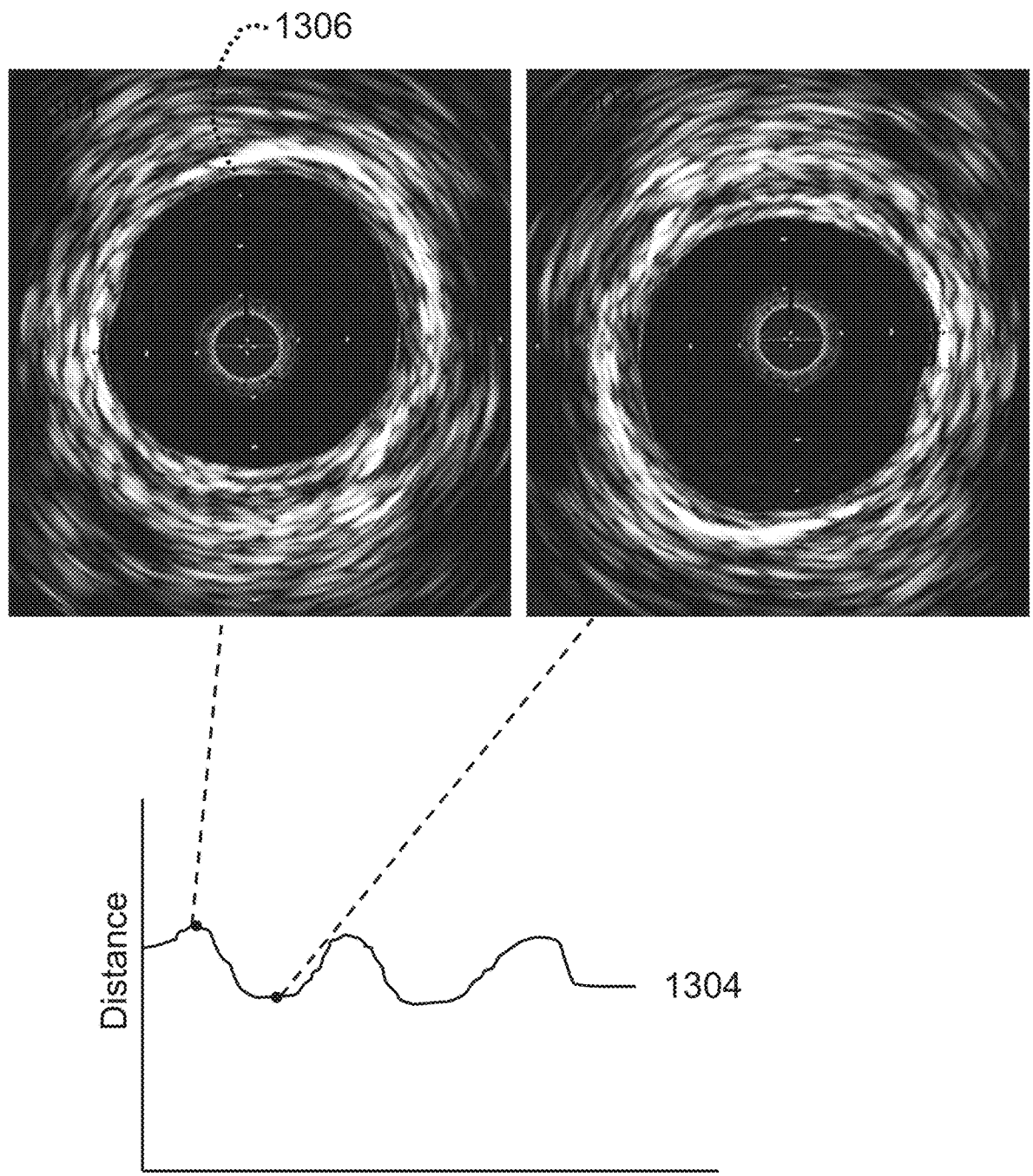
FIG. 13 shows an approach to extract the cardiac cycle from 2D intravascular image data (e.g. IVUS).
Figure 15:
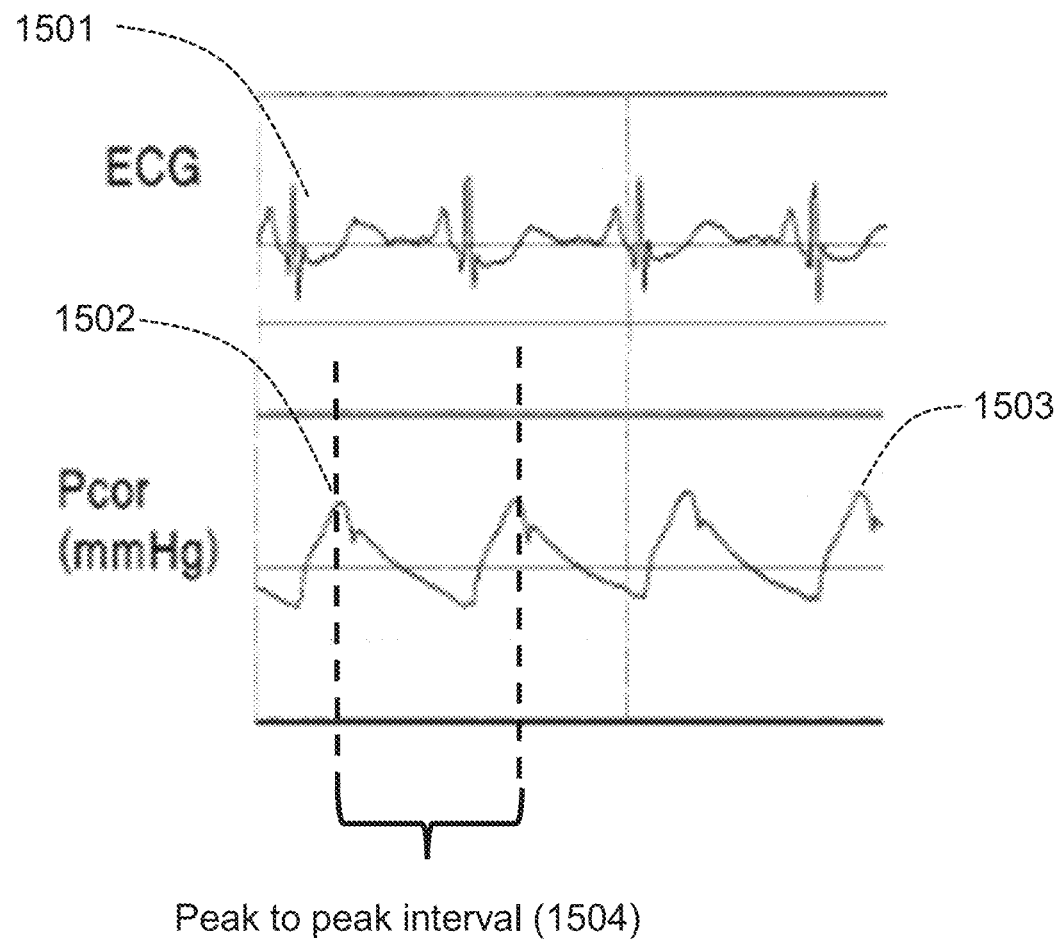
FIG. 15 shows the correlation of the pressure signal to the ECG signal.

Throughout this patent application, a radiopaque wire section is defined as either the radiopaque section or the intravascular sensor. The radiopaque wire section as used in the description of the present application can be used to identify the location of the intravascular measurements within the x-ray images. During the description of the method x-ray angiography will be used and refers to an x-ray acquisition of the vasculature, e.g. a coronary vessel tree, after administration of a contrast liquid resulting in visualization of the vasculature and other objects which are radiopaque. X-ray fluoroscopy used within current application refers to an x-ray acquisition without the use of contrast liquid and such will not visualize the vasculature. Within current application the term image or image frame refers to a single image and the term image sequence refers to a multiple images acquired over time and when used in relation to x-ray it comprises multiple frames covering one or more phases of the cardiac cycle and when used in relation to intravascular data comprises multi frames acquired during pullback of the intravascular device. The x-ray angiography image sequence may contain the contrast agent administration, and image frame which precedes the contrast agent administration will contain no contrast agent and thus no enhancement of the vasculature. The x-ray angiography image sequence and x-ray fluoroscopic sequence may comprise multiple frames covering one or more phases of one or more cardiac cycle. Throughout this application, a cardiac cycle is specific to a patient and is defined as the period in which covers one heartbeat of the patient. The cardiac cycle can for instance be defined as the period of time between successive R-tops within the ECG signal of the patient (see FIG. 7, 710), or as the period of time between successive peaks within the pressure signal of the patient (see FIG. 15, 1504). A phase refers to a moment (or period) of time within the cardiac cycle of the patient, e.g. end-systolic which defines the moment within the cardiac cycle in which the blood volume of the left ventricle is the lowest. Phase can be measured as an offset from R-top within the ECG signal of the patient as shown in FIG. 7 and its corresponding description or as an offset from a peak within the pressure signal of the patient as shown in FIG. 13 and its corresponding description. The term cardiac cycle information as used throughout this application refers to information like start of the cardiac cycle, end of the cardiac cycle or a specific phase within the cardiac cycle.

Figure 1:
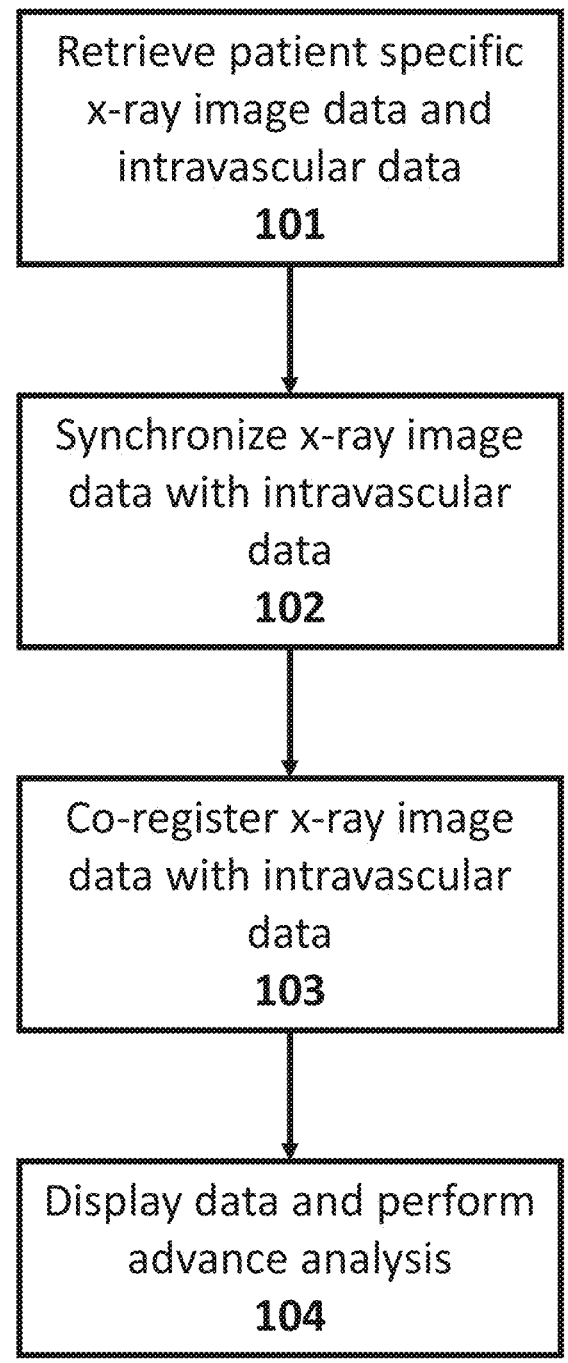
FIG. 1 shows a flow chart of a method for determining a dynamic coronary roadmap in accordance with an embodiment herein.

FIG. 1 shows a flow chart illustrating the operations according embodiments herein. The operations employ an imaging system capable of acquiring and processing two-dimensional image sequences of a vessel organ (or portion thereof) or other object of interest and one intravascular system of acquiring intravascular data. For example, a single plane or bi-plane angiographic system can be used such to acquire the x-ray image data as those manufactured, for example, by Siemens (Artis zee Biplane) or Philips (Allura Xper FD). To acquire the intravascular data, for example an FFR system can be used as those manufactured, for example, by ACIST (ACIST RXi System) or Boston Scientific (Polaris system) or Philips (Core Mobile).

Figure 2:
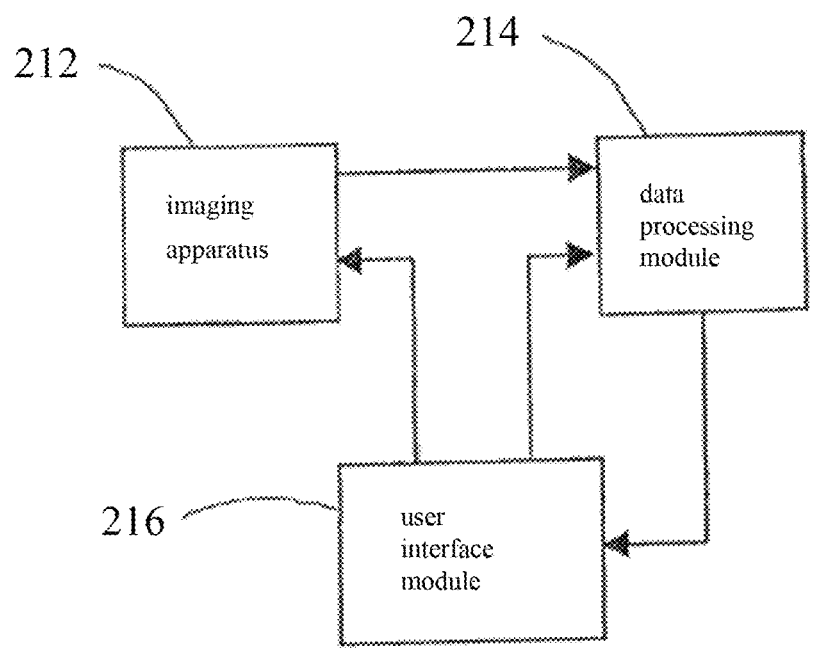
FIG. 2 shows a functional block diagram of an exemplary single plane angiographic system.

FIG. 2 is a functional block diagram of an exemplary single plane angiographic system, which includes an angiographic imaging apparatus that operates under commands from user interface module 216 and will provide data to data processing module 214. The single plane angiographic imaging apparatus 212 captures a two-dimensional x-ray image sequence of the vessel organ of interest for example in the postero-anterior direction. The single plane angiographic imaging apparatus 212 typically includes an x-ray source and detector pair mounted on an arm of a supporting gantry. The gantry provides for positioning the arm of the x-ray source and detector at various angles with respect to a patient who is supported on a table between the x-ray source and detector. The data processing module 214 may be realized by a personal computer, workstation, or other computer processing system. The data processing module 214 processes the two-dimensional image sequence captured by the single plane angiographic imaging apparatus 212 to generate data as described herein. The user interface module 216 interacts with the user and communicates with the data processing module 214. The user interface module 216 can include different kinds of input and output devices, such as a display screen for visual output, a touch screen for touch input, a mouse pointer or other pointing device for input, a microphone for speech input, a speaker for audio output, a keyboard and/or keypad for input, etc.

Figure 4A:
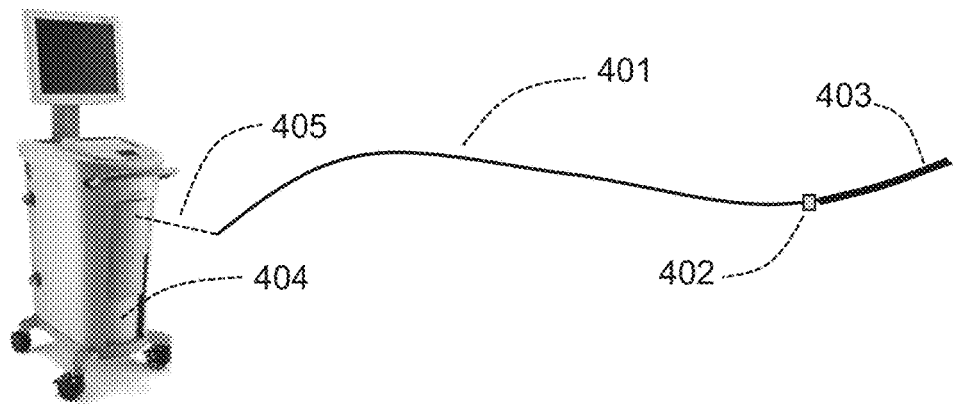
FIG. 4A shows a schematic illustration of a FFR measuring device.
Figure 27:
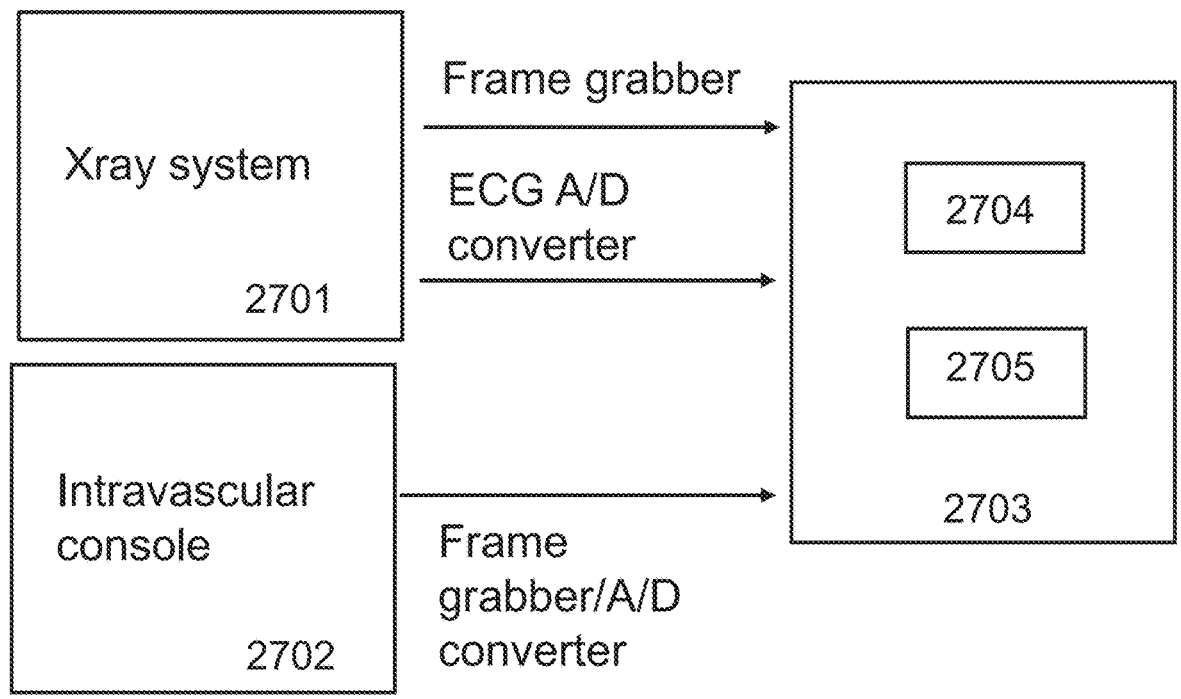
FIG. 27 shows the different high level system components in which the operations of current application can be integrated.
Figure 27:
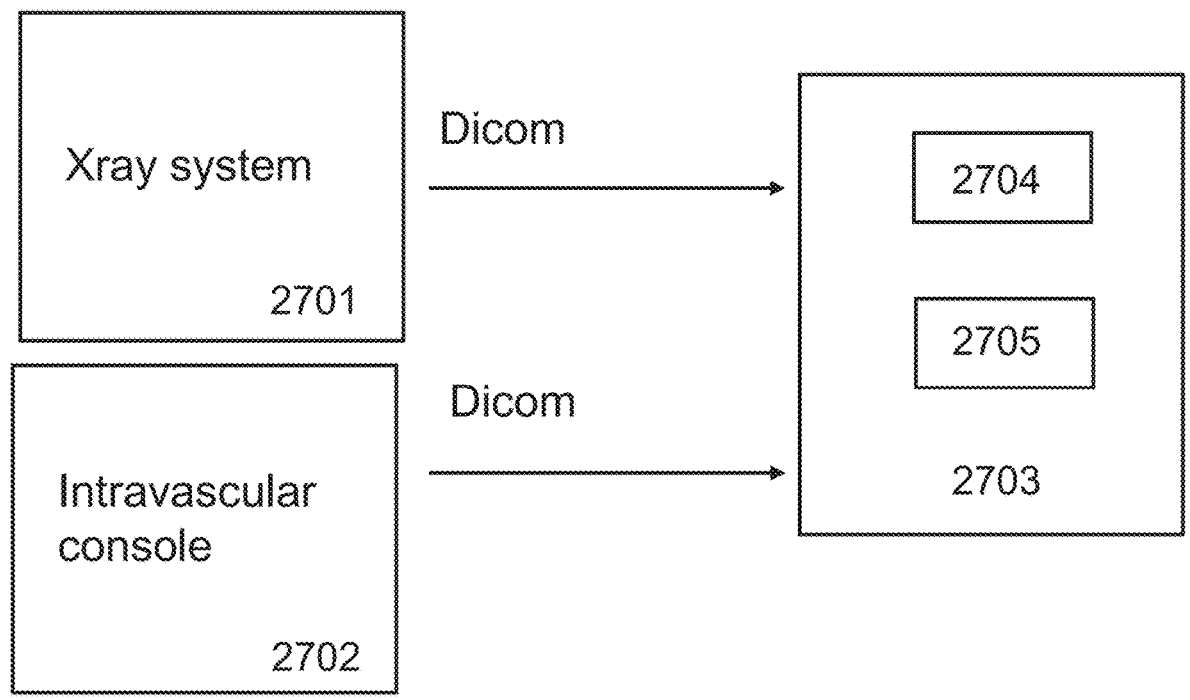

The angiographic imaging apparatus 2701 may be interfaced with the console 2702 of an intravascular system like the one shown, for example in FIG. 4A, either through a combination device 2703, as shown, for example, in FIG. 27, comprising a data processing module 2704 and a user interface module 2705 or directly by adapting the data processing module of the angiographic imaging apparatus to handle data coming from the intravascular system console and providing input devices capable of receiving intravascular data from such intravascular system console. Also parts of the intravascular system, particularly its data processing module, can act as a unit for handling data coming from the angiographic system console through input devices. In any of the possible configurations, the data processing module and the user interface module of the angiographic imaging apparatus, of the combination device or of the intravascular system console, or combination thereof, cooperate to carry out the operations of FIG. 1 as described below.

Such operations can also be carried out by software code that is embodied in a computer product (for example, an optical disc or other form of persistent memory such as a USB drive or a network server). The software code can be directly loadable into the memory of any of the data processing systems for carrying out the operations of FIG. 1. Such data processing system can also be physically separated from the angiographic system used for acquiring the images or the intravascular system used for acquiring intravascular data, for example may be included in a combination device as discussed above making use of any type of data communication for getting such angiographic images and intravascular data as input for such a combination device.

In the following example it is assumed that the x-ray imaging system has acquired and stored at least one two-dimensional image sequence of an object of interest and an intravascular system has acquired and stored intravascular data such as pressures, FFR/iFR/CFR data, IVUS/OCT images, or the like information.

An embodiment is now disclosed with reference to FIG. 1. The therein-depicted operations can, obviously, be performed in any logical sequence and can be omitted in parts. As it is an objective of the application to provide a select (e.g. optimal) workflow that can be used during the interventions, workflow example steps will also be referenced.

As can be seen in FIG. 1, the workflow comprises a number of steps. First at step 101 patient specific image data is retrieved. This patient specific image data contains both x-ray image data as well as data as acquired by an intravascular modality. Block 101 describes as an example that pressure data is used as acquired by a FFR measurement. The x-ray image data can be x-ray angiographic image data as well as x-ray fluoroscopic image data. In step 102 the pressure data is synchronized with the acquired x-ray image data, and in step 103 the x-ray image data is combined with the pressure data. This results in a co-registration of the x-ray angiographic image data with the pressure data as measured at the co-registered positions and is displayed or reported by step 104. In the following section, these steps are explained in more detail.

Figure 4B:
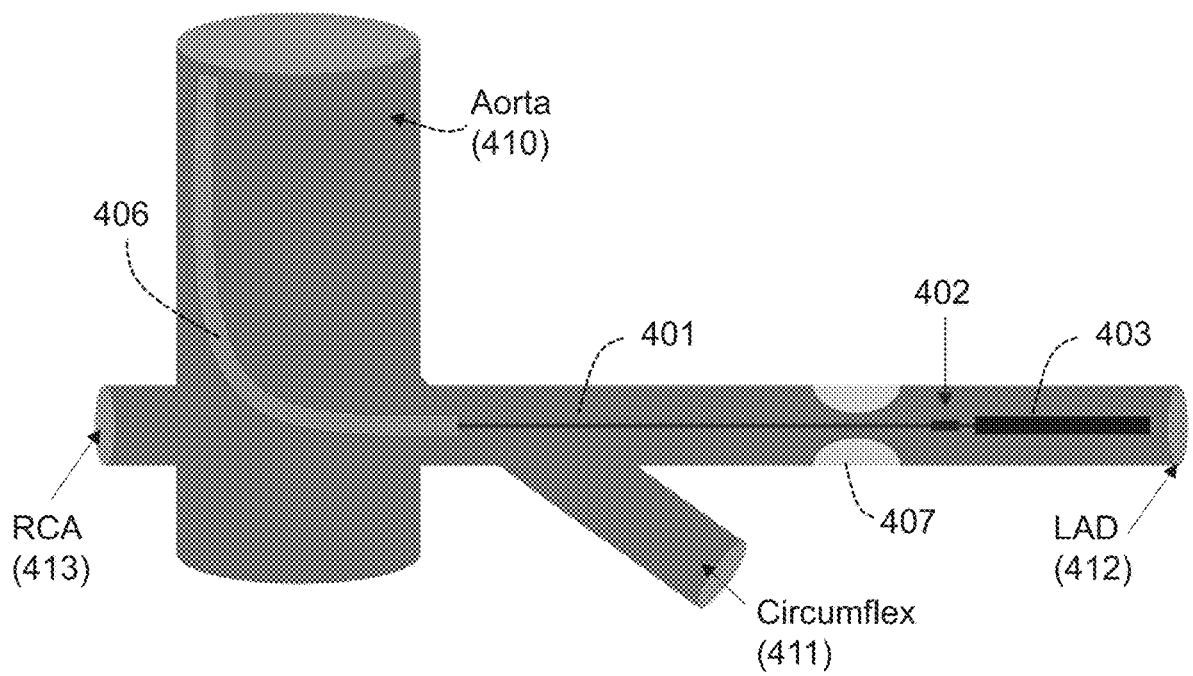
FIG. 4B shows a schematic illustration of a FFR wire inserted in the left coronary artery.
Figure 5A:
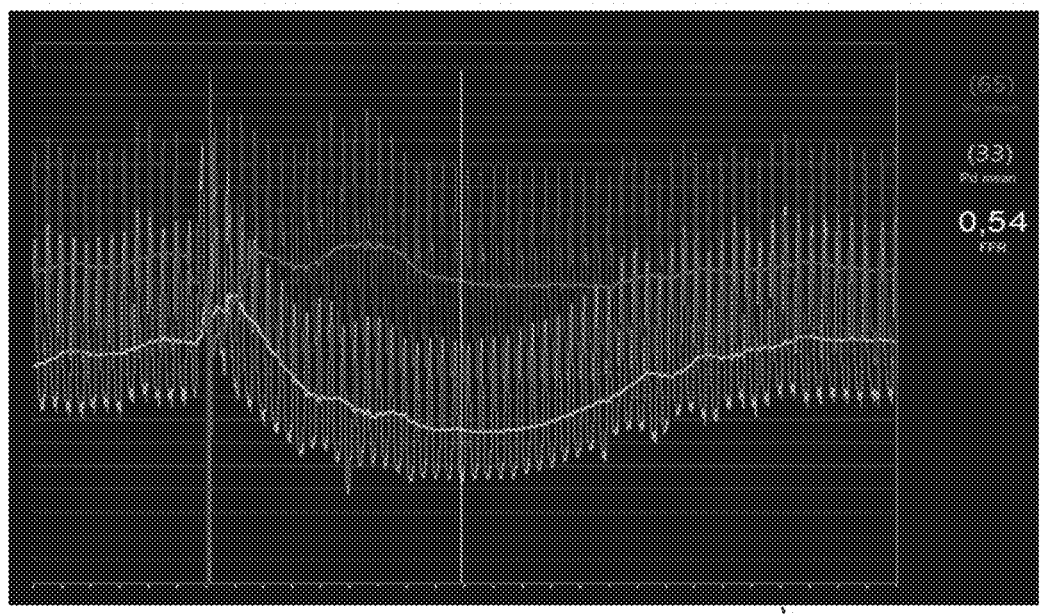
FIG. 5A shows an example of the measured pressure, where the x-axis represent time and the y-axis the pressure.
Figure 5B:
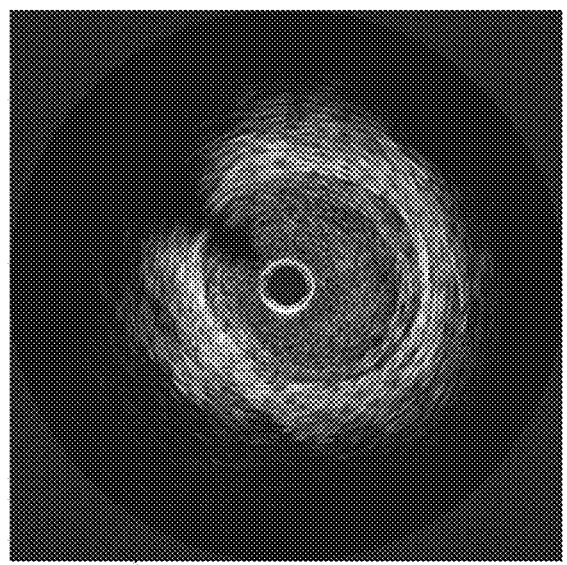
FIG. 5B shows an example of a single IVUS image frame and OCT frame.
Figure 5B:
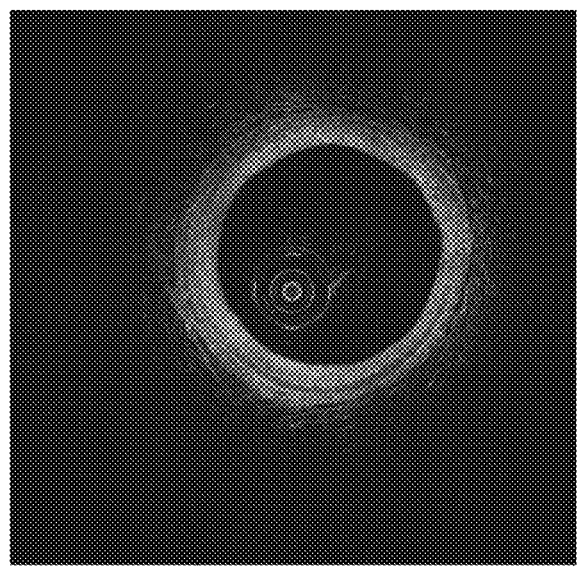
Figure 6:
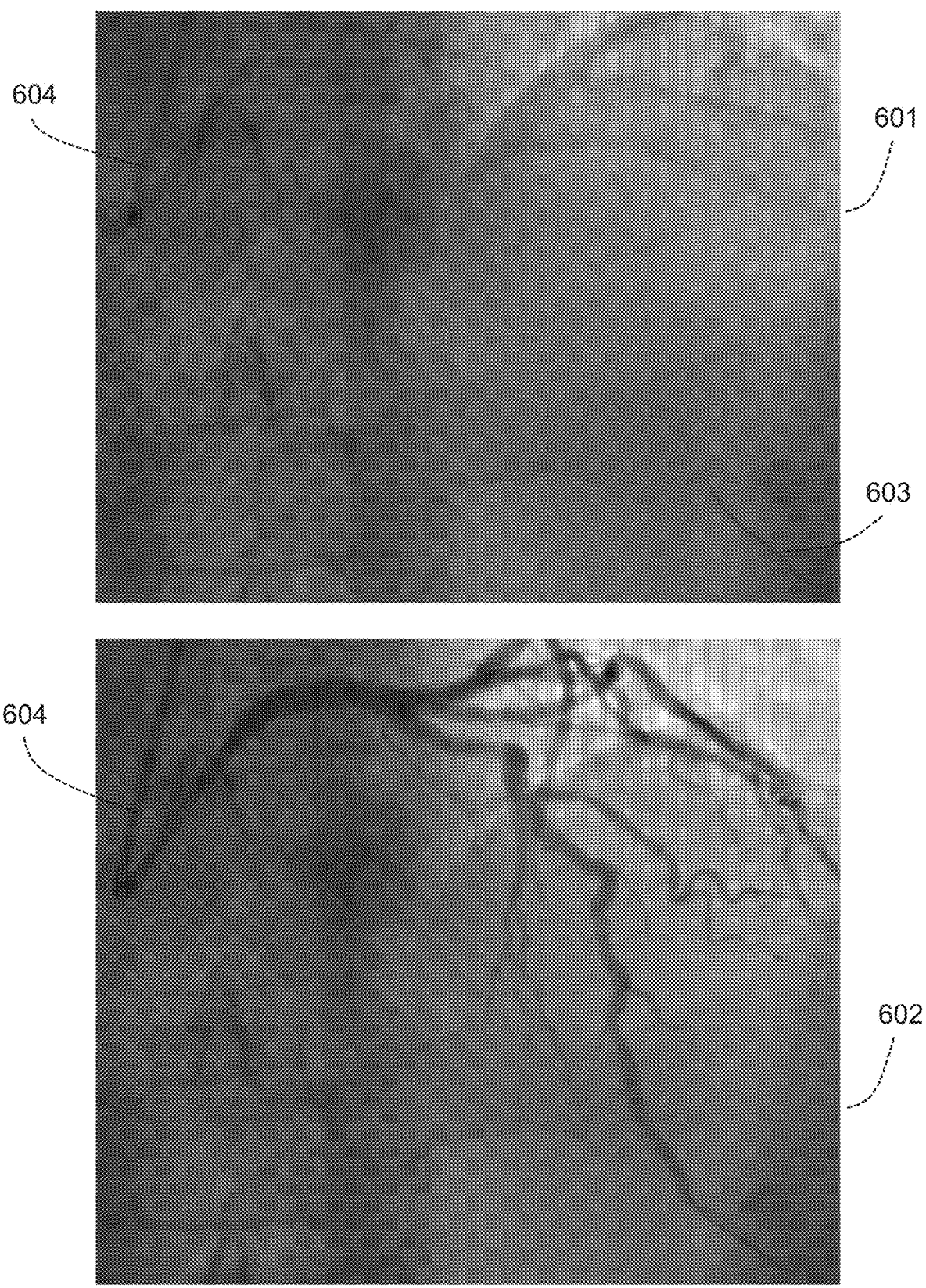
FIG. 6 illustrates an example of an x-ray fluoroscopic frame and an x-ray angiographic frame.

Step 101: Retrieve Patient Specific x-Ray Image Data and Intravascular Image Data The retrieval of the patient specific x-ray image data and intravascular data (e.g. pressure data or IVUS images) is described in detail by reference to FIG. 3. The patient specific x-ray image data and intravascular data is retrieved during X-ray coronary angiography. This is a common step of a PCI procedure or a diagnostic x-ray angiographic procedure. An example of an x-ray angiographic image is provided by 602 within FIG. 6 which shows the left coronary artery and 601 of FIG. 6 shows an example of a fluoroscopic x-ray image acquired at the same x-ray angulation of the same patient. Within picture 601 of FIG. 6, the intravascular wire (e.g. FFR wire) is inserted in the left coronary artery and the radiopaque marker of the intravascular wire (e.g. FFR wire) is visible (603). FIG. 4A and FIG. 4B illustrates in more detail the specifics of an intravascular system and in the example of FIG. 4A and FIG. 4B a FFR system is illustrated. FIG. 4A shows a schematic illustration of a FFR measuring device. The FFR wire (401) is connected through an interface (405) with a console (404). The FFR wire is a very thin and flexible wire which is inserted through a standard diagnostic catheter (406, FIG. 4B). Typically, on the tip of the FFR wire a radiopaque material is present (403) allowing visibility during x-ray fluoroscopy. The pressure sensor (402) is located within a known distance to the radiopaque material (403). FIG. 4B shows a schematic illustration of a FFR wire inserted in the left coronary artery (LAD) 412, distal to a coronary obstruction (407). The diagnostic guiding catheter (406), which is inserted percutaneously through vascular system towards the aorta (410), is used the push the wire towards the desired location. In case measurements are required of the LAD (412) or circumflex (411), the guiding catheter is placed within the left coronary ostium, and incase measurements are required of the right coronary artery (RCA) 413, the diagnostic guiding catheter is placed that the right coronary ostium. Picture 501 of FIG. 5A shows an example of the measured pressure, where the x-axis represent time and the y-axis the pressure. Within 501, two pressure curves a visualized, one pressure curve is the pressure curve as measured with the FFR wire and representing the pressure within the coronary artery (Pd), the other pressure curve is measured by a pressure device connected to the diagnostic guiding catheter and represents the pressure within the aorta (Pa). As mentioned before, the inventive concept would mainly be disclosed by using FFR as example of an intravascular imaging modality, but the teachings are not limited to FFR as in intravascular imaging modality as such they are also applicable to other intravascular modalities such as, for example, IVUS, OCT, iFR, CFR and the like. Within FIG. 5B an example of a single IVUS image frame is shown by 502 and 503 shows an example image frame of within an OCT image sequence. Both images (502 and 503) represents one image frame, as a cross sectional image of the vessel, within an IVUS/OCT pullback.

Figure 3:
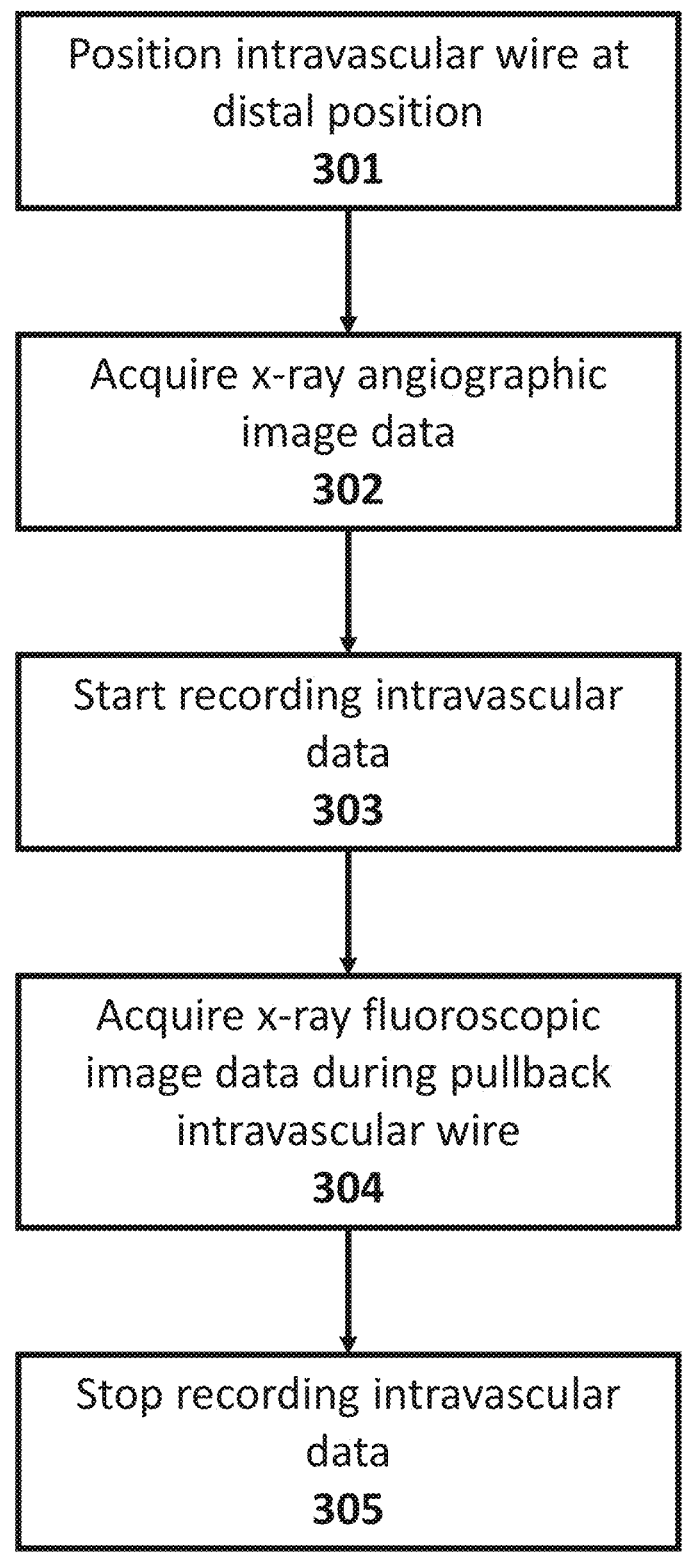
FIG. 3 shows a flow chart for retrieval of patient specific x-ray image data and intravascular data.

Within step 301 of FIG. 3, the intravascular wire (e.g. pressure wire) is positioned at a distal location within the vessel of interest. An example of an x-ray fluoroscopic image acquired after the pressure wire is positioned is presented by 601 within FIG. 6. The radiopaque part of the intravascular wire (603 illustrates a FFR wire) is clearly visible, and no visible information of the vessels is present within 601.

Within step 302 of FIG. 3, an x-ray angiographic image is acquired. This image or image sequence will be as reference image for the co-registration. This will be explained in more detail during the description of step 103 from FIG. 1. An example of such x-ray angiographic image is presented by 602 of FIG. 6. This angiographic image is acquired with same angulation as image 601, and the left coronary vessels are clearly visible due to the administration of a contrast liquid through the guiding catheter (604).

At step 303 of FIG. 3, the recording of the intravascular modality start, and in case of FFR the recording of the pressure data start. In case the intravascular modality is FFR, maximal coronary blood flow (hyperemia) is induced by injecting of for instance as adenosine or papaverine.

Next in step 304 an x-ray fluoroscopic image sequence is acquired which covers the pullback of the intravascular imaging device, for example a pullback of the FFR pressure wire. The pullback covers several cardiac cycles, and is depending on the pullback speed, patient heartbeat and the pullback length. Typically, the pullback covers between 8-40 cardiac cycles. FIG. 7 shows three x-ray fluoroscopic frames (701, 702 and 703) from an acquired x-ray fluoroscopic image sequence. The radiopaque marker (material) of the intravascular wire is visible (704) as well as the guiding catheter (705) within the x-ray fluoroscopic image frames and has been enhanced for illustration purpose. Each x-ray fluoroscopic frame is acquired within an arbitrary moment (phase) of the cardiac cycle, as illustrated by 706, 707 and 708 within an electrocardiogram (ECG) signal (709) representing a cardiac cycle (710). The start of the cardiac cycle is for example the R-top (711) and all acquired x-ray frames (706, 707 and 708) represent a phase within the cardiac cycle (710), which is given by the time offset with respect to the start of the cardiac cycle (710) for the acquisition of the respective x-ray frame. Note that the ECG signals in FIG. 7 represents the ECG period corresponding to the image frame (to the right of the visualized ECG signal) and do not need to be from the same cardiac cycle. In general, the ECG signal is acquired together with the image data and stored together in a DICOM, which allows identification of each image frame with respect to ECG signal. This information is further used during the explanation of step 102 of FIG. 1. In case the ECG signal is not acquired or not available, the time (moment or phase) of a particular image frame within an image sequence with respect to the cardiac cycle can be extracted from the image data itself. This method is based on motion extracted from features within the x-ray fluoroscopic image sequence like the catheter and is further described by step 1002 of FIG. 10 or from motion extracted from the intravascular image sequence and is further described by step 1003 of FIG. 10.

Finally, at step 305 of FIG. 3, after the pullback of the intervascular device stops, the recording of the intravascular modality stops.

Step 102: Synchronize X-Ray Image Data with Intravascular Data

Figure 8:
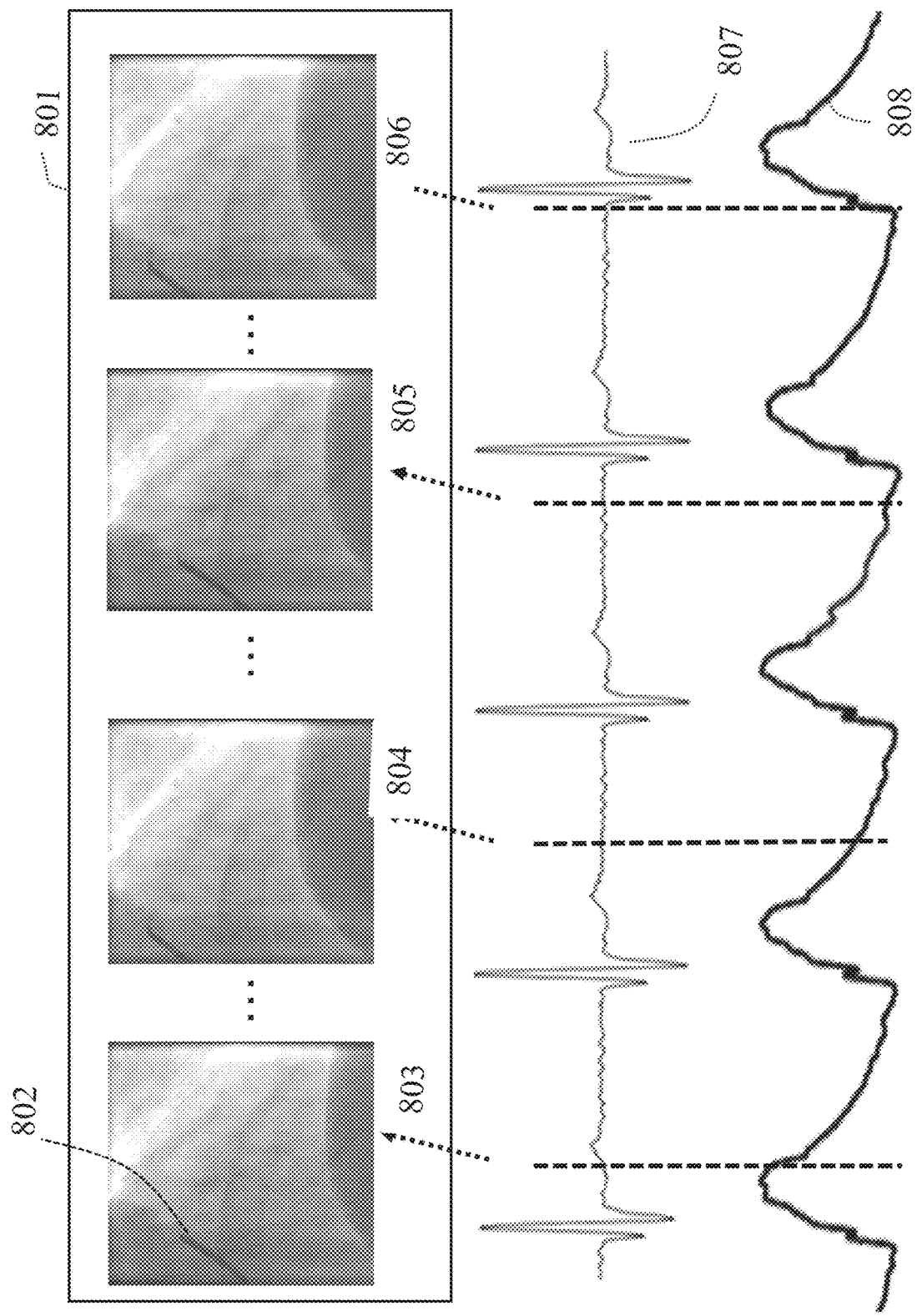
FIG. 8 shows the approach to synchronization of the intravascular data with the x-ray fluoroscopic frames.

Within step 102 the intravascular data (e.g. pressure data) is synchronized with the image data as retrieved within step 101 and in more detailed with reference to the flowchart of FIG. 3. As described by the flowchart of FIG. 3, the intravascular data is retrieved during the pullback of the intravascular imaging device. The pullback of the intravascular imaging device is captured by the x-ray fluoroscopic image sequence (304). The synchronization of the intravascular data (e.g. pressure data, IVUS/OCT images) involves the temporal alignment of the intravascular data with the x-ray fluoroscopic frames within the x-ray fluoroscopic sequence and is illustrated by FIG. 8, in which the intravascular data represents pressure data. FIG. 8 shows a typical example of an x-ray fluoroscopic image sequence, in which 801 illustrates a number of sequential x-ray image frames within such a sequence, and 807 shows the corresponding ECG signal and pressure data signal (pressure waveform) 808. The phase within the cardiac cycle in which the x-ray fluoroscopic image frames (803, 804, 805 and 806) are acquired with respect to the ECG signal (807) and pressure waveform (808) is illustrated in FIG. 8.

Figure 9:
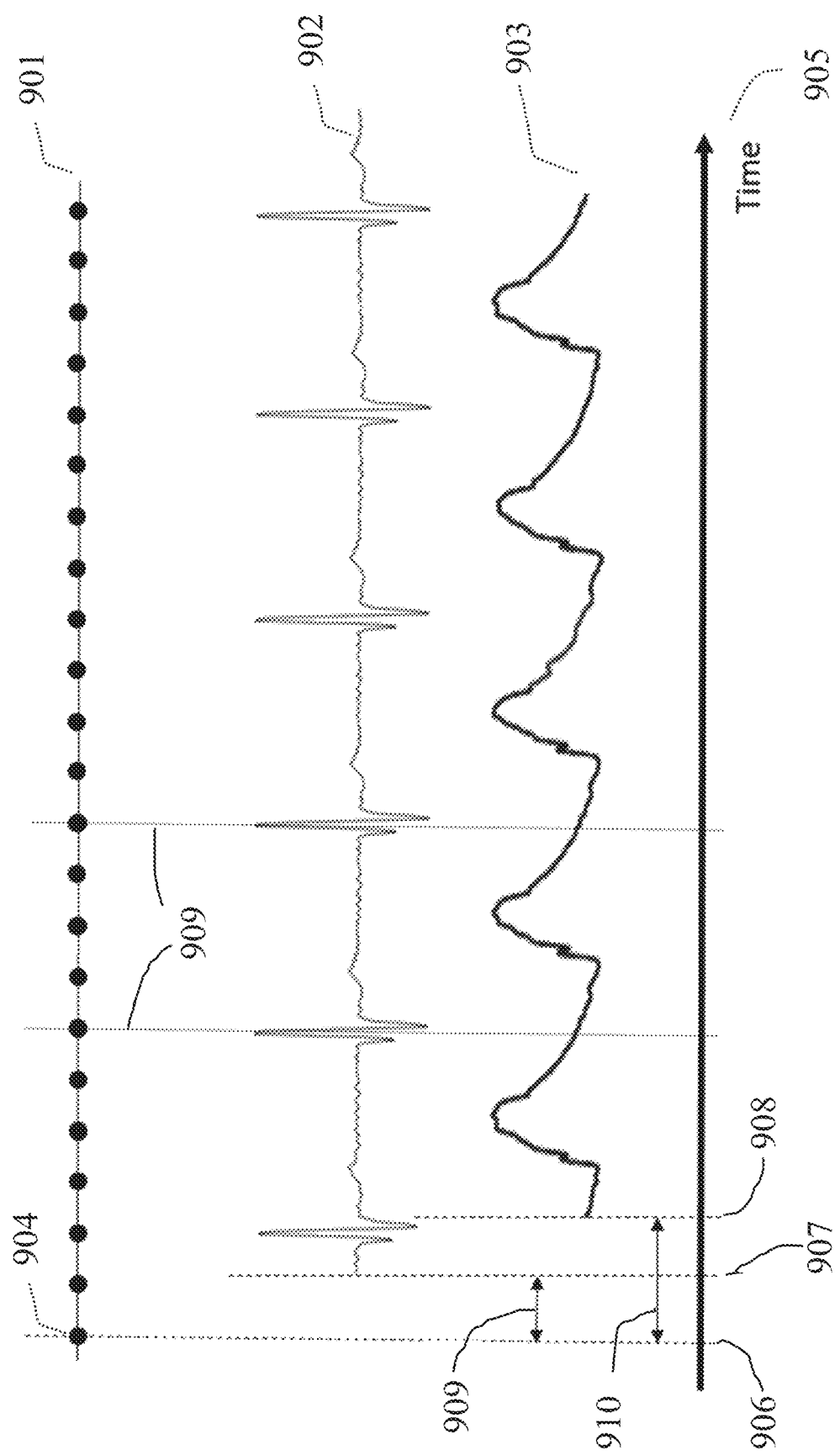
FIG. 9 shows the approach in synchronization in which the real world time relation between the retrieved image data is available.

Within step 102, next to synchronizing the data, cardiac cycles are extracted, and a specific cardiac phase is defined within each cardiac cycle. This information will be used by step 103 to reduce the cardiac motion. There are two situations that differ in approach to synchronize the data. In case the real world time relation between the retrieved image data (x-ray image data, ECG data and intravascular image data) is not known with respect to each other, a synchronization algorithm is needed to align the cardiac cycles within the retrieved image data. In case the real world time relation between the retrieved image data is known with respect to each other, a direct synchronization can be performed. Above is visualized by FIG. 9 in which the second situation is illustrated. Within FIG. 9, 905 represents the real world time, in which the real world time is defined as the local time. The x-ray fluoroscopic image sequence is represented by 901 in which each successive frame is represented by a dot (904, which represent the first frame of the x-ray fluoroscopic sequence). The ECG signal is represented by 902 and the intravascular image data is represented by 903 and in this example the intravascular image data represents a pressure signal. At real world time (906), the acquisition x-ray fluoroscopic image sequence starts, and at real world time 907, the acquisition of the ECG signal starts. The real world start time of the pressure data is represented by 908. Since the start time in real world time is known of each, a (one-time) calibration needs to be performed to extract possible delays in the signals (909, 910). The situation illustrated by FIG. 9 is typically for a system configuration in which the retrieved image data is physically collected by one or multiple system as illustrated by FIG. 27. The term physically collected in this context refers to the creation of the image data in memory in which the knowledge of the real world time present. For instance, when the x-ray fluoroscopic image data is digitalized by means of a frame grabber by a system, the system knows when this data was digitalized with respect to real world time. The same is true for obtaining ECG signal with an A/D converter and obtaining the intravascular image data, either with a frame grabber or A/D converter, depending on the type of intravascular image device.

In case the ECG signal and the x-ray fluoroscopic image data is retrieved by means of file transfer (e.g. DICOM file), the real world time alignment between the ECG and the respective x-ray fluoroscopic image frame is present, however, the real world time alignment with the intravascular image data is absent. Furthermore, the ECG data may not be available in this situation, or the ECG data is retrieved separately by means of an A/D converter. The situation is typical when the x-ray image data and intravascular image data are received by separate files (for example DICOM)

and have no real world time connection with each other as illustrated in FIG. 27. It may also the case when the image data is provided in memory lacking real world time information relative to each other.

Real World Time Relation Between the Retrieved Image Data is Unknown

In case the real world time relation between the retrieved image data is not available, the synchronization of the intravascular image data with the x-ray fluoroscopic image data is further explained by reference to the flowchart of FIG. 10. Since the presence of an ECG signal is not always guaranteed, the flowchart of FIG. 10 includes an alternative step 1002 to extract the cardiac cycle based on the retrieved x-ray fluoroscopic image data (step 101) instead of the ECG data.

Figure 10:
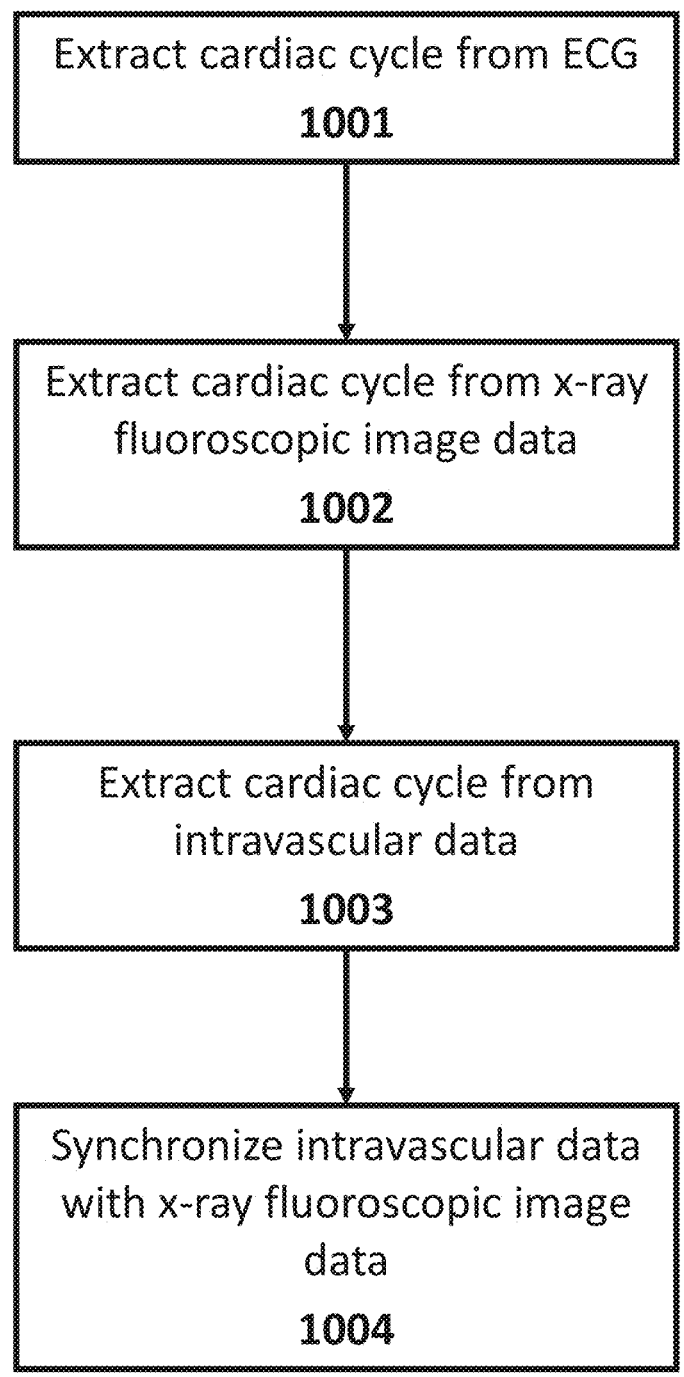
FIG. 10 shows a flow chart for synchronization of the intravascular data with the x-ray fluoroscopic frames in case the real world time is unknown.

The first step of FIG. 10, step 1001, involves the extraction of the cardiac cycles based on the ECG signal. In case the ECG signal is not available the workflow continues at step 1002. The cardiac cycles can be determined/identified by aligning the acquired ECG signal with a generic template of the ECG signal, in which this generic template consist of one or one cardiac cycles, and calculate a correlation measure as minimization measure for the alignment algorithm. This generic template of the ECG signal can, for example, be derived from large population of patient data. The amount of correlation is calculated, for example, by calculating cross-correlation to provide a measure for periodicity, and may be used to assess the reliability of the ECG signal. Another option to extract periodicity from the acquired ECG signal by performing Fourier analysis on the acquired ECG signal. Detection of specific features within the ECG signal can be used to determine cardiac cycles, as for instance ECG QRS-complex detection algorithms as for example taught by Pan et al., "*A Real-Time QRS Detection Algorithm*", IEEE Transactions on Biomedical Engineering. BME-32 (3): 230-236. Each detected QRS-complex can be used as the start of a new cardiac cycle. Optionally, the reliability of the ECG signal can be assessed based on the cardiac cycle identification algorithms, as for instance ECG QRS-complex detection algorithms as for example taught by Pan et al., "*A Real-Time QRS Detection Algorithm*", IEEE Transactions on Biomedical Engineering. BME-32 (3): 230-236. A predefined threshold can be used to assess if the ECG signal is reliable or not. In case the ECG signal is considered to be unreliable the workflow continues at step 1002.

If the ECG signal is present and the ECG signal is defined to be reliable, the workflow continues as step 1003.

Figure 12:
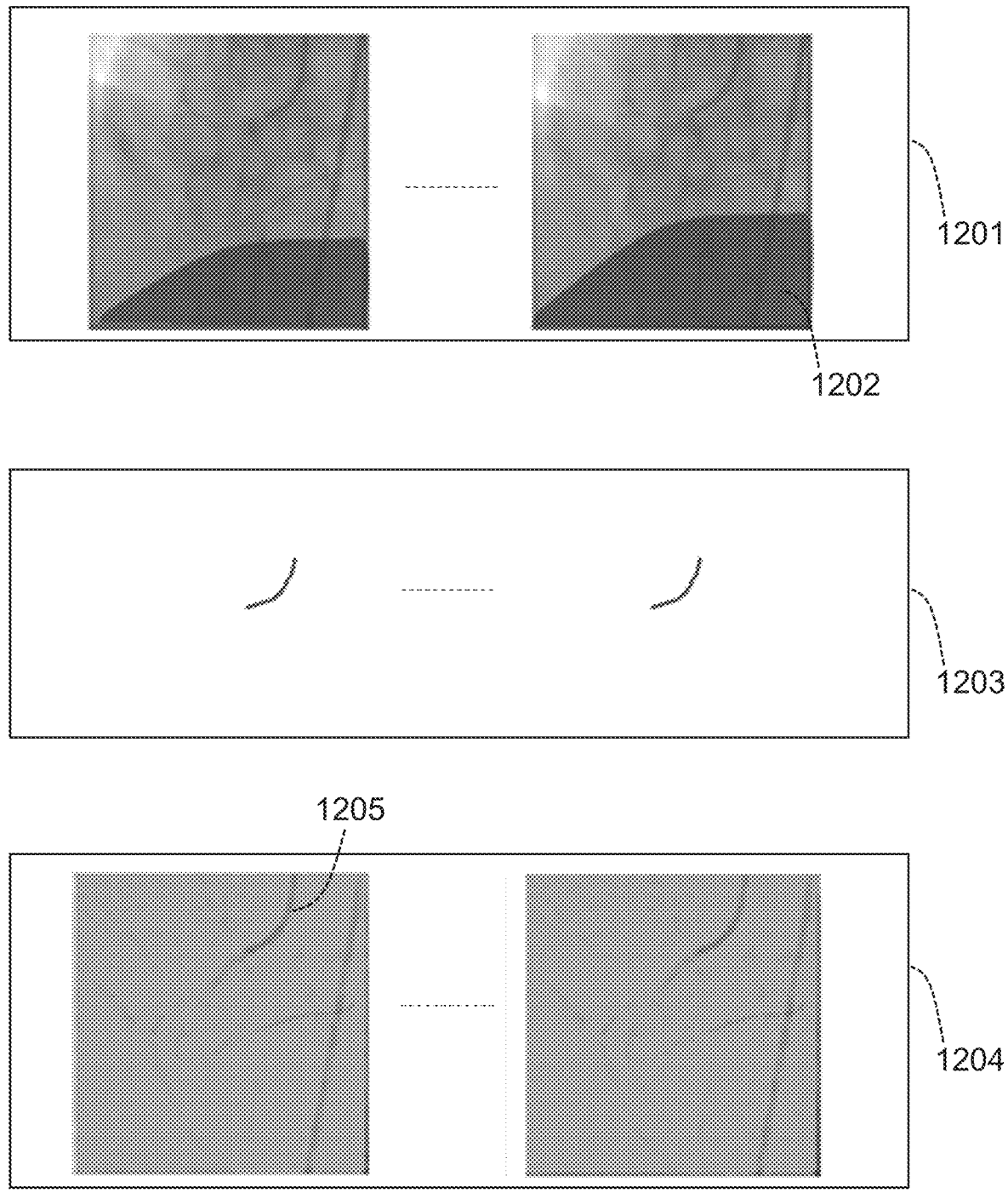
FIG. 12 shows some approaches to extract the cardiac cycle from x-ray fluoroscopic image sequence.

At step 1002, the cardiac cycles are extracted from the x-ray fluoroscopic image data. This step is only applicable when no (reliable) ECG data is available. In general, coronary motion exists of cardiac motion due to contraction of the heart, breathing motion due to respiration of the patient and patient motion due to patient movement. In case the cardiac cycle is extracted from x-ray fluoroscopy as retrieved by step 304 FIG. 3, the catheter tip being visible in the image sequence can be used. The catheter tip is located in the ostium of the coronary tree and will therefore experience motion due to the contraction of the heart. From this motion the cardiac cycle can be extracted. To extract the cardiac cycle, only the motion of the coronary artery which can be extracted from the (guiding) catheter tip should be considered. Therefore, cardiac motion surrogate extraction by means of analyzing the motion pattern of objects representing cardiac motion, such as catheter tip, provides information on the cardiac cycle within an x-ray fluoroscopic image sequence. Within FIG. 12, 1201 represent a number of successive x-ray image frames (two) within an x-ray fluoroscopic image sequence. The movement of the diaphragm 1202 is visible within the successive x-ray image frames 1201. One approach to extract the cardiac cycle is illustrated by 1203 of FIG. 12. Picture 1203 represent the extracted (detected) catheter from the image frames of 1201. This detection can be performed without any user interaction, using various known image segmentation techniques, like thresholding, convolution, correlation techniques or other automatic segmentation techniques. For instance, the catheter can be detected by applying a Frangi vesselness filter (Frangi et al., "*Multiscale Vessel Enhancement Filtering*", Medical Image Computing and Computer-Assisted Intervention—MICCAI 1998 Lecture Notes in Computer Science 1496/1998:130) followed by a non-maximum suppression (for example as taught by Li et al., "*Skeletonization of gray-scale image from incomplete boundaries*", Proceedings of the International Conference on Image Processing, ICIP 2008, October 12-15). Also machine learning approaches can be used for catheter tip detection as for instance disclosed by U.S. patent application Ser. No. 16/739,718, in which a method is disclosed for catheter tip detection using a deep learning based Bayesian filtering approach. In summary the method of U.S. patent application Ser. No. 16/739,718, to be included herein by reference, models the likelihood term of Bayesian filtering with a convolutional neural network and integrates it with particle filtering in a comprehensive manner, leading to more robust tracking. Optionally user input can be used for image segmentation or indicating the catheter tip position. Based on a catheter segmentation a function $f(frame)$ is build that contains the displacement value between each successive frame. By applying a Fourier transform, both the cardiac motion can be separated from the breathing motion or patient motion.

Within FIG. 12, picture 1204 illustrates another approach to extract the cardiac cycle. In this situation, the images are processed in such a way that structures which does not represent cardiac motion are eliminated and structures with cardiac motions, such as the catheter, are enhanced. In this situation, cardiac motion becomes the major source of intensity change in the image sequence and can be further analyzed with methods having source decomposition capability such as principal component analysis. First, the x-ray fluoroscopic image sequence 1201 is processed in such a way that only structures with cardiac motion such as catheters are enhanced (1205). This can be performed by using a layer separation method as taught by Hao et al., "*Vessel Layer Separation in X-ray Angiograms with Fully Convolutional Network*", Proc. SPIE 10576, Medical Imaging 2018: Image-Guided Procedures, Robotic Interventions, and Modeling, or by Ma et al., "*Layer separation for vessel enhancement in interventional x-ray angiograms using morphological filtering and robust PCA*", Workshop on Augmented Environments for Computer-Assisted Interventions 2017, Springer. pp. 104-113 or by Ma et al., "*Automatic online layer separation for vessel enhancement in x-ray angiograms for percutaneous coronary interventions*", Med Image Anal. 2017 July; 39:145-161. Principal component analysis is typically used for dimension reduction. It transforms a multivariate dataset to a new orthogonal coordinate system such that most variance of this dataset could be represented by a few coordinates. Hence, reducing its dimension is normally achieved by preserving only a few coordinates in the new coordinate system without losing much information. Principal component analysis is used on the post processed images (1204) to obtain principal components for the image sequence. Representing a frame of the sequence with an n×n matrix, each pixel in such matrix is concatenate into a single column vector $x^i$, whose size is D×1, where $D=n^2$. Thus, a sequence consisting of N frames is represented as a D×N matrix $X=[x^1, \ldots, x^N]$. Seeking the principal components of X is equivalent to computing the eigenvectors of covariance matrix X, which is a D×D matrix. As D is usually a large number and in our case D>>N, eigen analysis is applied to the N×N matrix $X^TX$.

$$E = X\tilde{E}\nabla^{-1} \quad \text{(equation 1)}$$

where E is the D×N matrix of eigenvectors of $XX^T$, $\tilde{E}$ is the N×N matrix of eigenvectors, and $\nabla$ is the N×N diagonal matrix of eigenvalues of $X^TX$. Next, the post processed sequence (1204) is projected on the first principal component $e_1$ by computing:

$$p = X^T e_1 \quad \text{(equation 2)}$$

where $e_1$ is the first column of E representing the direction of the largest variance and p is a N×1 projection vector. So each frame in such sequence is represented by an element in vector p. The assumption underlying the described approach is that cardiac motion is the major source of variation in these sequences (1204) where respiratory motion and patient motion are eliminated. Therefore, p is used as the cardiac motion surrogate representing the cardiac cycle motion within the image sequence 1101.

The motion surrogate function f(frame) or p can now be used to determine cardiac cycles. This can for example be done by correlation of the displacement function with a template motion function. This template can, for example, be extracted from a database of signals already matched with the cardiac cycle and breathing motion for example manually by an expert. Other option is to identify repetitive patterns within the displacement function, each repetition should resample a cardiac cycle.

From step 1001 or 1002 the cardiac cycles are extracted that can be linked to the x-ray fluoroscopic image data because the ECG and x-ray fluoroscopic image data are coupled. To be able to synchronize the x-ray fluoroscopic image data with the intravascular data, the cardiac cycle information of the intravascular data needs to be determined and can then be aligned with the cardiac cycle information of the x-ray fluoroscopic data.

In step 1003 the cardiac cycles are extracted from the intravascular image data. The intravascular image data can be either intravascular image data like OCT, IVUS or the like (intravascular 2D image data) or intravascular data can be pressure data from FFR, iFR, or the like (intravascular 1D image data, also referenced to in the present disclosure as non-imaging data).

Extraction of Cardiac Cycles from Intravascular 2D Image Data

Figure 14:
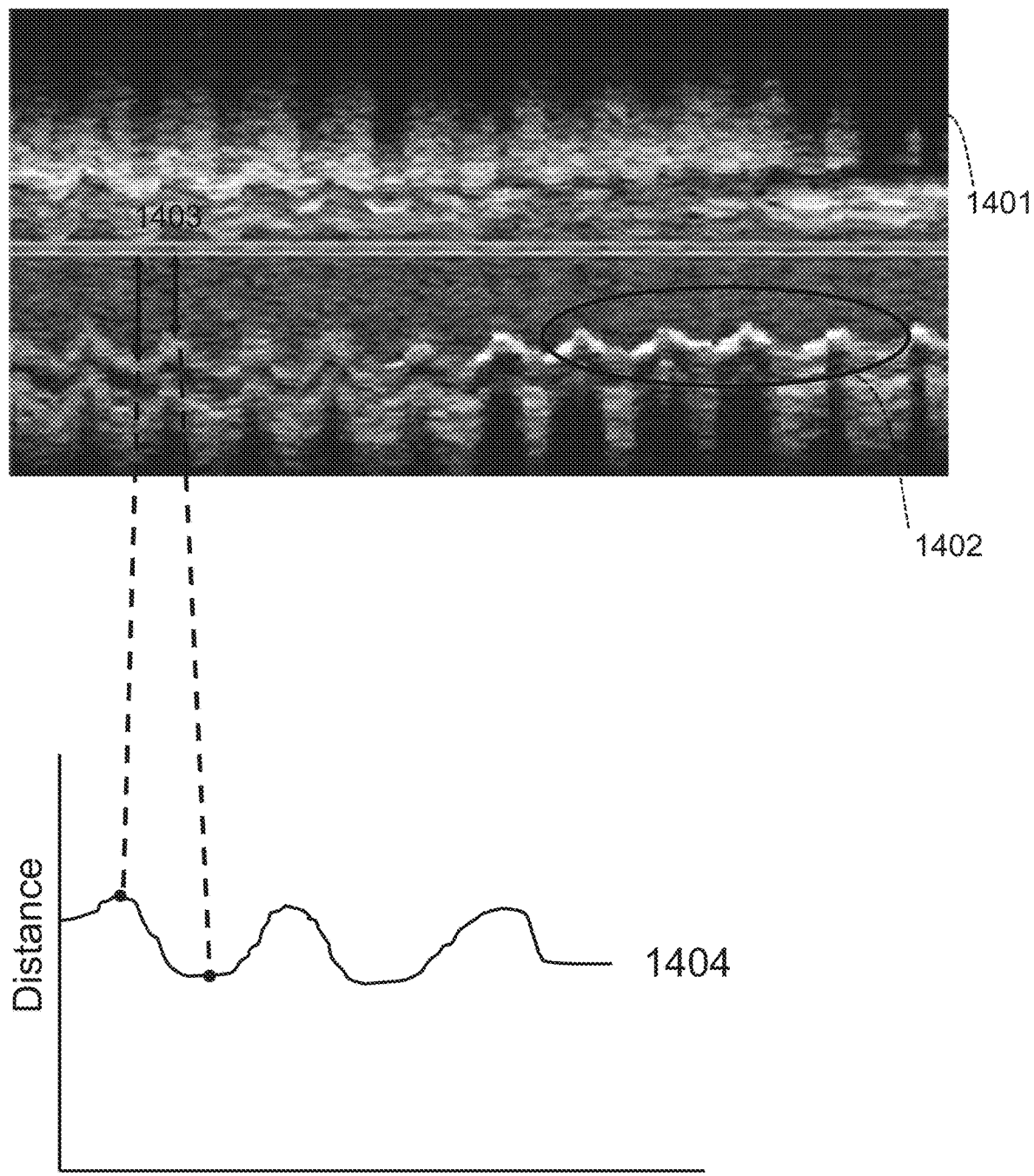
FIG. 14 shows another approach to extract the cardiac cycle from 2D intravascular image data (e.g. IVUS).

In case the intravascular imaging as performed during step 304 of FIG. 3 represents in a 2D image such as OCT, IVUS or the like, the cardiac cycles can be extracted from this intravascular image data. Within intravascular imaging like OCT, IVUS, or the like, cardiac motion induces a transient motion between the imaging probe and the lumen border during the acquisition. This motion of the imaging probe with respect to the lumen border can be used to extract the cardiac cycle from intravascular images. This can for example be done by calculating the distance (1303, FIG. 13) from the imaging probe (1305) to lumen border (1306) within each cross sectional image frame (1301, 1302). Combining the distances calculated in each cross-sectional image frame into a graph 1304 provides information about the cardiac cycle. From this distance graph cardiac cycle information can be calculated similar to the techniques as explained for determining this information for guiding catheter. Instead of using the cross-sectional images the same technique can be applied on a longitudinal image created from all cross-sections of the pullback. An example of a longitudinal IVUS image is given by 1401 in FIG. 14. The transient motion between imaging probe and lumen wall is revealed in the longitudinal image 1401 by the saw-tooth shape of the lumen-vessel wall border indicated by 1402. By evaluating the lumen border position (saw-tooth shape) in the longitudinal image information about cardiac motion is provided. Other solutions are revealed in literature like evaluating a signal created from pixel values within a region of interest within the intravascular image frames. Matsumoto et al., "*Cardiac phase detection in intravascular ultrasound images*", SPIE Proceedings, Medical Imaging 2008: Ultrasonic Imaging and Signal Processing, Vol. 6920, 69200D, evaluated four signals created from a ROI, which is the entire ultrasound image for Matsumoto et al., the Average intensity (AI), Average Intensity Density(AID), Cross-correlation coefficient (CC) and Mutual information (MI).

Extraction of Cardiac Cycles from Intravascular 1D Image Data

In case the intravascular imaging as performed during step 304 of FIG. 3 represents in a 1D image such as FFR, iFR, CFR or the like, the cardiac cycles can be extracted from this 1D image data which typically represents a pressure signal. To be able to extract cardiac cycles a periodic signal is needed having a periodicity matching the cardiac cycle. The retrieved pressure signal can be used in case the intravascular imaging modality represent a pressure imaging modality such as FFR, iFR or CFR. Because the heart is the pumping blood throughout the human body by consecutive contraction and relaxation of the heart chambers, the blood pressure will vary in a cycle which correlates to the cardiac cycle. During contraction blood is pushed into the vessels resulting in a rise of the blood pressure and during relaxation the heart chambers are filled with blood and the pressure in the vessels decreases. Therefore, the pressure data is also a periodic signal and correlates to the cardiac cycle. An illustration of a pressure signal is given in 1502 FIG. 15 which also illustrates the correlation to the ECG signal (1501, FIG. 15). First optionally, preprocessing of the signal can be performed to remove possible baseline shifts or drift in the signal. This can for example be done by means of high pass filtering of the pressure signal. A periodic cardiac cycle can be found by detecting periodic features within the signal, like for instance peaks in the pressure signal (1503) which can be detected by instance as thought by Shalbaf et al., "*A Real-Time Algorithm for Extraction of Heart Beat in Invasive Blood Pressure*", Biomed 2008, Proceedings 21, pp. 103-106. The peak to peak interval (1504 FIG. 15) can then be correlated to the cardiac cycle based on for example Berne R. B., Levy M. N. (2001), '*Coronary Circulation*', in *Cardiovascular Physiology*, $8^{th}$ Edition, Mosby/Elsevier, p227-240.

At step 1004, the intravascular data is synchronized with the x-ray fluoroscopic image data. This step involves the temporary alignment between the intravascular image data with the x-ray fluoroscopic image sequence; align to the same real world time. This is done by aligning all cardiac cycles extracted from ECG (as a result of step 1001) or x-ray fluoroscopic image data (as a result of step 1002) with the cardiac cycles determined in the intravascular data (as a result of step 1003). This is further explained by reference to FIG. 16. Within FIG. 16, the ECG signal (1601) is used, but it can be replaced by the catheter tip motion signal, as determined in step 1002, in case ECG is for instance absent or unreliable. Within FIG. 16, the cardiac cycle as extracted from the intravascular image data (as a result of step 1003) is shown by 1602, and in the example provided a pressure signal is shown as the case of a FFR, iFR or CFR intravascular system. Within the ECG signal (1601) and intravascular signal (1602) a specific cardiac phase needs to be detected for each cardiac cycle (1603, 1604, 1605 and 1606), it needs to be the same phase for both signals, e.g. end-systolic phase. The specific cardiac phase is further identified as the selected phase.

Figure 16:
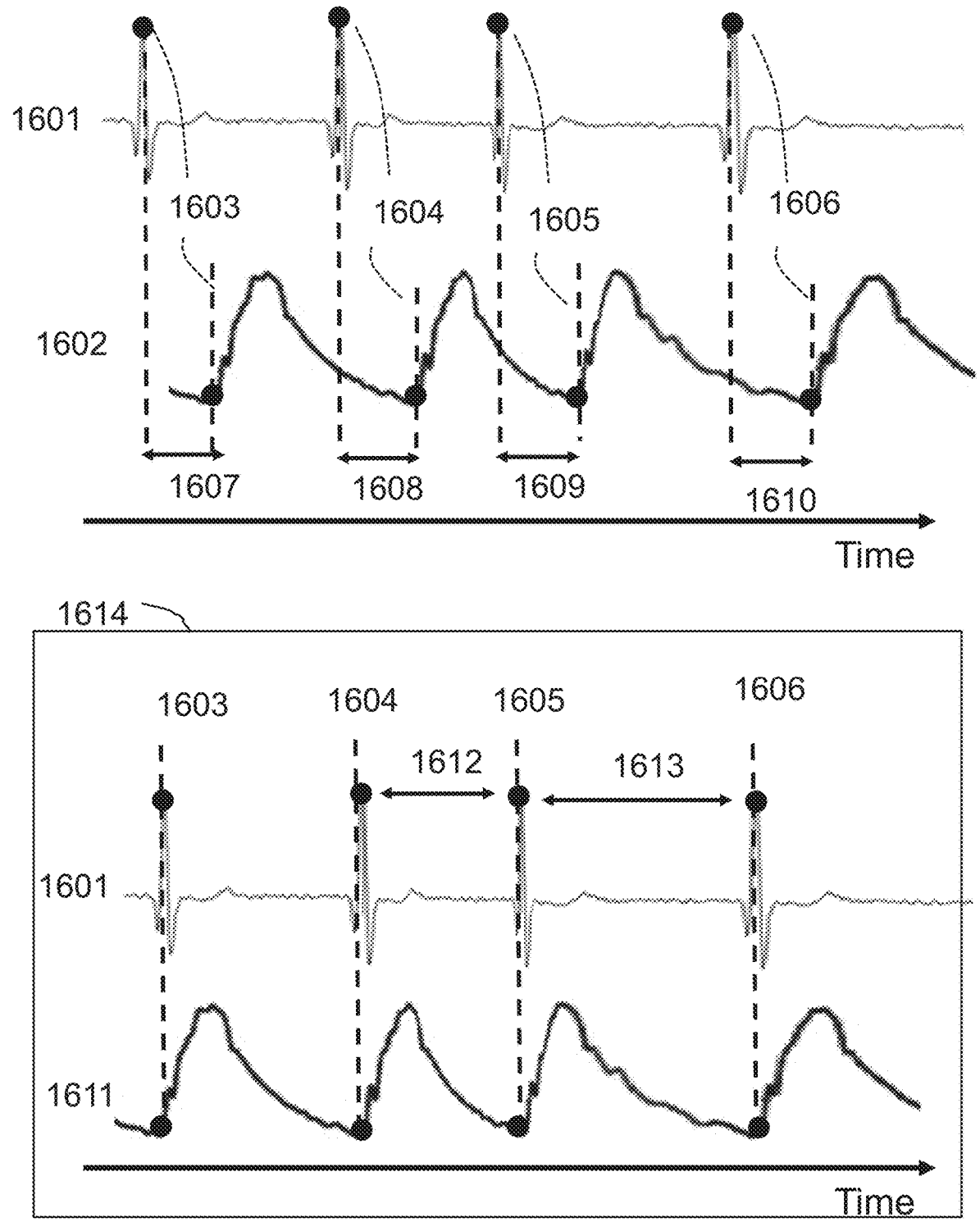
FIG. 16 shows an approach to synchronization of the intravascular image data with the x-ray fluoroscopic frames in case the real world time is unknown.

Then by shifting one signal over the time-axis until the time difference between the detected phases of the two signals, as illustrated by 1607, 1608, 1609 and 1610, is minimal. This principle works since there is always some variability between the periods of the cardiac cycles, meaning that the duration of each cardiac cycle slightly varies in time. This is illustrated by FIG. 16 in which the cardiac cycle period of 1612 is smaller than the period of the next cardiac cycle 1613. The picture 1614 visualized the result of this step, in which the 1D pressure signal (1602) is aligned (1611) to the 1D ECG signal (1601).

Figure 11:
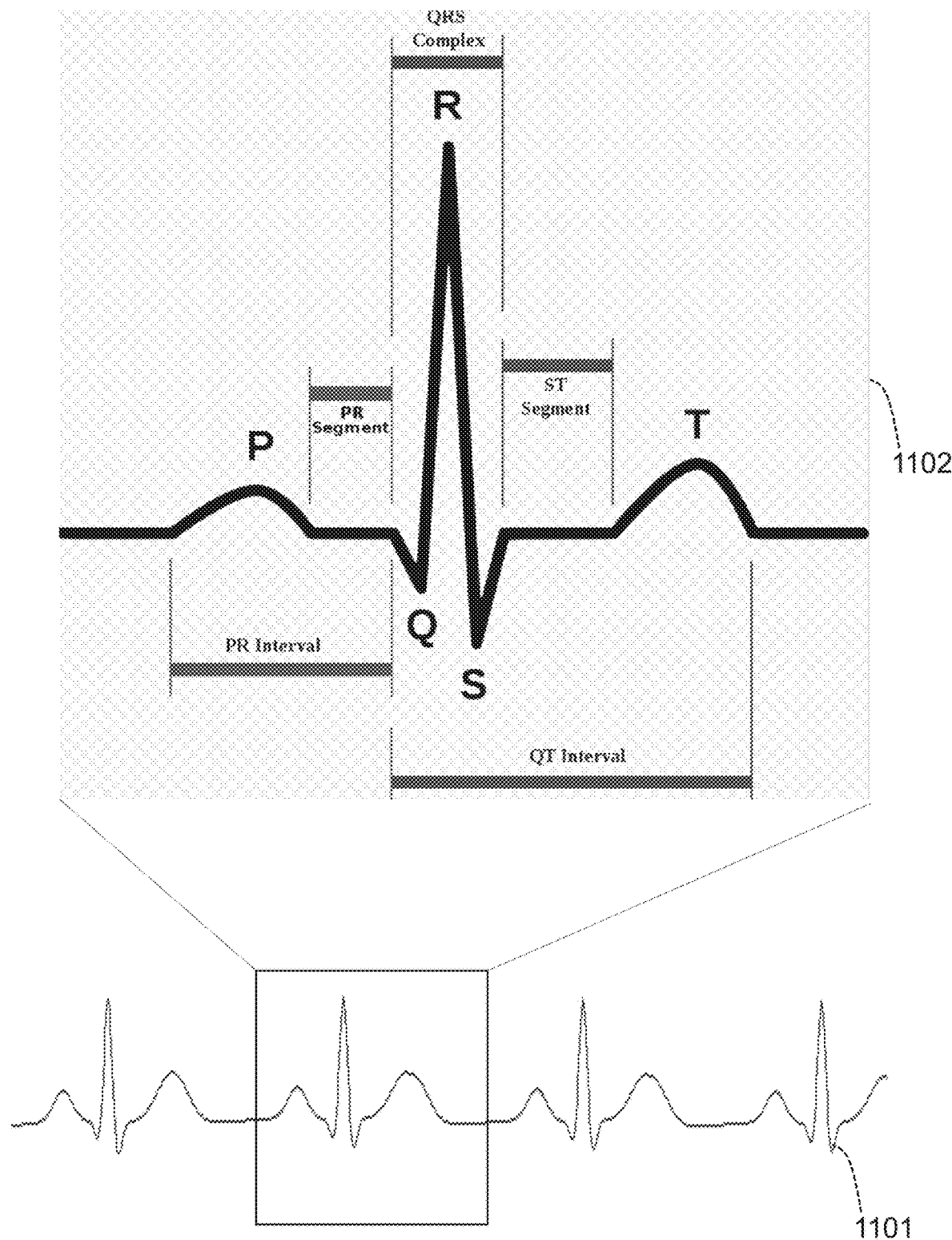
FIG. 11 shows an example of an ECG signal with unique phases within the cardiac cycle.

To identify the selected phase, the 1D signals (as created by step 1001, 1002 and 1003) are used. All these 1D signals can be processed and analyzed using similar techniques, since they are all represent repetitive signals with a frequency based on the cardiac cycle. Each of these 1D signals contains features that can be recognized within the signal which belongs to unique phases of the cardiac cycle. For example, within the ECG signal R-top, T-top, QRS complex, QT interval, etc. as illustrated in FIG. 11. Coronary motion and pressure signals also contain repetitive characteristic features, like peaks, within each cardiac cycle. For example, the coronary motion throughout the cardiac cycle is investigated by Lu et al., "*Coronary Artery Motion During the Cardiac Cycle and Optimal ECG triggering for Coronary imaging*", Investigative Radiology 2001; 36:250-256. The teachings by Lue et al. can, for example, be used to link motion features within each cycle to a cardiac phase.

To identify these unique features that correspond to specific phases of the cardiac cycle several techniques can be used. First template signals can be used that can be correlated to the 1D signals. A template signal in which the cardiac phase is known can be aligned to the 1D signal by shifting and stretching the template signal using template matching or correlation algorithms using metric like cross-correlation as minimization metric. These template signals can be generated from patient populations in which for example the cardiac phase is annotated by a clinical expert or obtained from studies like Lu et al., "*Coronary Artery Motion During the Cardiac Cycle and Optimal ECG triggering for Coronary imaging*", investigative Radiology 2001; 36:250-256.

Another technique is for example by finding peaks within the signal (for example the R top see FIG. 10 or highest pressure in pressure signal). When the relation of the peak with respect to cardiac phase is known, for example from literature or clinical expert the cardiac cycles can be assigned with a cardiac phase.

When the x-ray fluoroscopic image data and the intravascular data are matched, it is possible to select x-ray fluoroscopic image frames from a specific cardiac phase and their corresponding intravascular data/Real World Time Relation Between the Retrieved Image Data is Known Referring back to step 102 of FIG. 2. In case the real world time relation between the retrieved image data is available, the synchronization of the intravascular data with the x-ray fluoroscopic image data is further explained by reference to the flowchart of FIG. 18.

Figure 18:
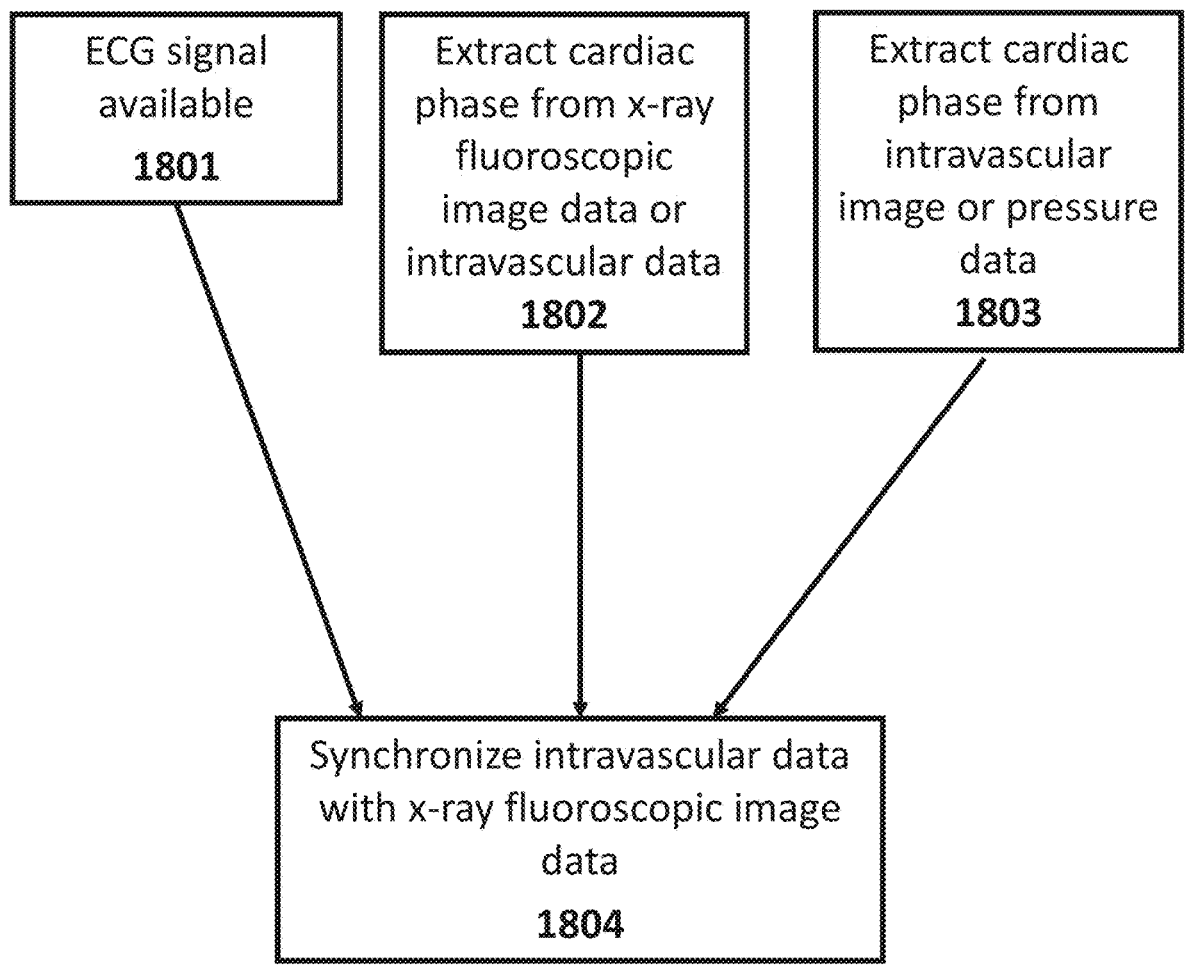
FIG. 18 shows a flow chart for synchronization of the intravascular data with the x-ray fluoroscopic frames in case the real world time is known.

In case start of image/signal acquisitions are known relative to each other, the signals/images can be synchronized based on the time difference between starts of acquisitions and the sample and/or frame rate, this workflow is illustrated by FIG. 18. This synchronization of the different signals 1801, 1802 and 1803 is done in step 1804.

As described before, FIG. 9 illustrates the case in which the real world time relation between the retrieved image data is available. The x-ray fluoroscopic image sequence is represented by 901 in which each successive frame is represented by a dot (904, which represent the first frame of the x-ray fluoroscopic sequence). The ECG signal is represented by 902 and the intravascular image data is represented by 903 and in this example the intravascular image data represents a pressure signal. At real world time (906), the acquisition x-ray fluoroscopic image sequence starts, and at real world time 907, the acquisition of the ECG signal starts. The real world start time of the pressure data is represented by 908. Since the start time in real world time is known of each, a (one-time) calibration needs to be performed to extract possible delays in the signals (909, 910).

Determination of a specific cardiac phase (selected phase) within each cycle is also part of step 102. Because all signals are synchronized it is only needed to determine the cardiac phase (selected phase) in all cardiac cycles for only one signal (901, 902 or 903). This can be done by similar method as described before as for instance by de description of step 1004.

Step 103: Co-Register x-Ray Image Data with Intravascular Data

Figure 19:
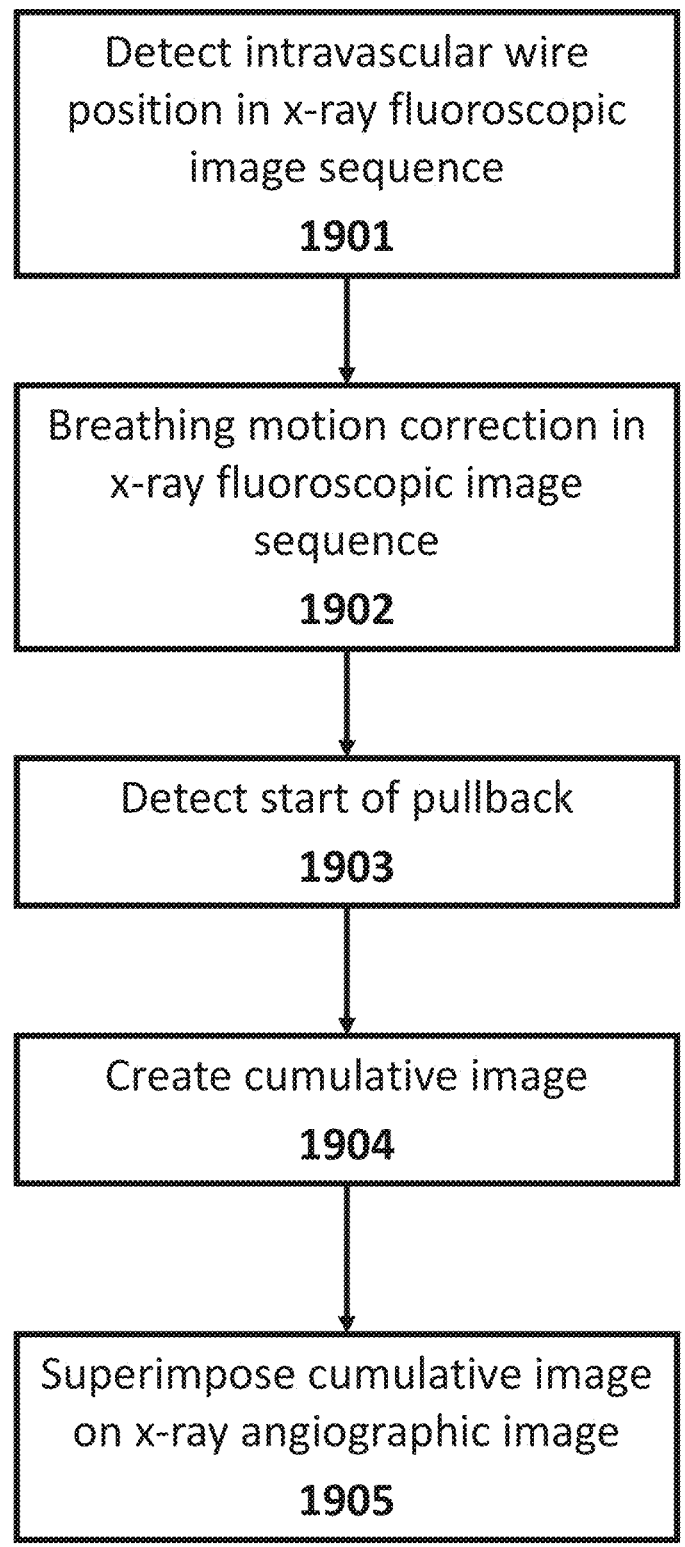
FIG. 19 shows a flow chart of the steps to co-register the x-ray image data with the intravascular data.

Within step 103 the actual co-registration of the intravascular image data with the x-ray image data takes place. FIG. 19 presents a flowchart of the steps to co-register the x-ray image data with the intravascular image data. On high level, a cumulative image (1904) is created at a single phase of the cardiac cycle from the x-ray fluoroscopic image sequence which represents the radiopaque wire section during pullback of the intravascular wire (see 2006 of FIG. 20). This cumulative image is registered (1905) with an x-ray angiographic image frame representing the same cardiac cycle as used to generate the cumulative image. Since we know the temporal alignment between the intravascular image data and the x-ray image data (as a result of step 102), co-registration of the intravascular image data with the x-ray image data can be established. All the steps from the flowchart of FIG. 19 will now be explained in more detailed.

At step 1901 of FIG. 19 the radiopaque wire section of the intravascular wire as visible within the x-ray fluoroscopic image frames (704 of FIG. 7) is detected to obtain spatial information about the position of the radiopaque wire section during the duration of the x-ray fluoroscopic image sequence, which covers the pullback of the intravascular device (e.g. pressure wire) (step 304 of FIG. 3). The detection of the radiopaque wire section may be done on all frames within the x-ray fluoroscopic image sequence, but should at least be performed on all frames which has the same phase within a cardiac cycle as determined by step 102 of FIG. 1. By using the frames at a specific phase within a cardiac cycle, like for instance the r-top, cardiac motion is minimized making the calculation of the cumulative image in step 1904 feasible. Detection of the radiopaque wire section can be done fully automatic, i.e. without user interaction, or semi-automatic using various known image segmentation techniques, like for instance thresholding, convolution, correlation techniques or other automatic segmentation techniques. An example of a (semi) automatic segmentation is by manually identifying the radiopaque wire section in one frame, and propagate this location to the remaining frames by means of image processing techniques for example as taught Zang et al., "*Cascade Attention Machine for Occluded Landmark Detection in 2D X-Ray Angiography*", January 2019 IEEE Winter Conference on Applications of Computer Vision (WACV). Also machine learning approaches can be used for radiopaque wire section detection for example as taught by Wagner et al, "*Deep learning based guidewire segmentation in x-ray images*", SPIE Proceedings, Medical Imaging 2019: Physics of Medical Imaging, 1094844 (1 Mar. 2019). Optionally user input can be used for image segmentation or of the radiopaque wire section.

At step 1902 correction of breathing motion, and possible patient motion, as present in the x-ray fluoroscopic image sequence, optionally takes place. As mentioned before, coronary motion exists of cardiac motion due to contraction of the heart, breathing motion due to respiration of the patient and patient motion due to patient movement. The correction of cardiac motion is performed by only selecting x-ray fluoroscopic image frames at a specific single phase of the cardiac cycle (see also step 1901 and 1904). Within step 1902, breathing motion, and possible patient motion correction is based on the assumption that the catheter tip (FIG. 20, 2007) remains at the same anatomical position within the coronary tree, allowing to use this position as a landmark to map the frames onto each other. The method involves the detection of the catheter tip position within all the frames of the x-ray fluoroscopic image sequence, or at least in all x-ray fluoroscopic image frames which has the same phase within a cardiac cycle as determined by step 102 of FIG. 1. Next, the catheter tip motion can be determined and used to eliminate the breathing motion and/or patient motion. For example, in case the catheter tip location in Frame A (2003) and frame B (2004) is known, the displacement of the catheter tip can be calculated, the inverse of this displacement can be applied to image B to eliminate the breathing motion between image A and B. Catheter (tip) detection can be achieved using techniques like machine learning as for instance disclosed by U.S. patent application Ser. No. 16/739,718, in which a method is disclosed for catheter tip detection using a deep learning based Bayesian filtering approach. In summary the method of U.S. patent application Ser. No. 16/739,718 models the likelihood term of a Bayesian filtering approach by a convolutional neural network and integrates it with particle filtering in a comprehensive manner, leading to more robust tracking. Another method to detect the catheter (tip) based on convolutional neural network is taught by Ambrosini et al., "*Fully automatic and real-time catheter segmentation in x-ray fluoroscopy*", International Conference on Medical Image Computing and Computer-Assisted Intervention 2017, Springer. pp. 577-585. Catheter (tip) segmentation can also be based on more conventional segmentation techniques as used for example used for pressure wire detection step 1901 (FIG. 19). Optionally, image registration techniques for example as taught by Maintz et al., "*An overview of Medical Image registration Methods*", in symposium of the Belgian hospital physicists association: 1996, can be used to eliminate small errors. For example, in case the entire pressure wire is visible the wire (tip) can be registered onto the wire of another image frame.

Optionally, at step 1903 the start of the pullback of the intravascular wire is detected. This step allows that the co-registration only considers intravascular image data during the pullback of the intravascular wire. The start of the pullback of the intravascular wire is accomplished by examination of the movement curve along the frames in the x-ray fluoroscopic image sequence of the detected radiopaque wire section (step 1901) which has been corrected for breathing motion as a result of step 1902. The movement curve is created by computing the absolute distance of the detected radiopaque wire section between a first x-ray fluoroscopic image frame (reference frame) and all remaining x-ray fluoroscopic image frame within the x-ray fluoroscopic image sequence. The time (or x-ray fluoroscopic frame) in which the pullback of the intravascular wire starts is defined as the moment in which the movement curve exceeds for instance a predefined threshold.

Figure 20:
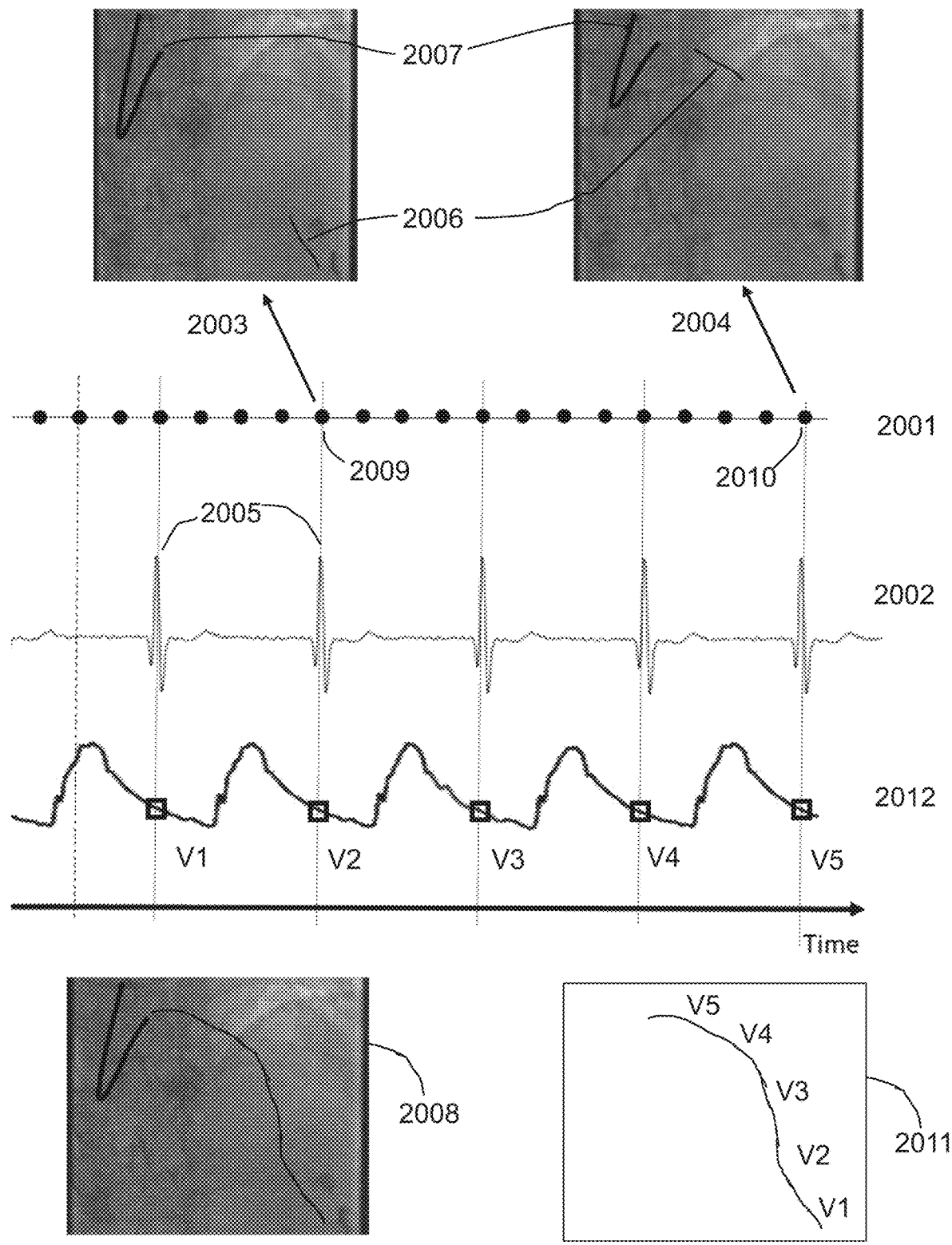
FIG. 20 shows an approach to generate the cumulated image.

At step 1904, a cumulated image is created which represents the radiopaque wire section during pullback of the intravascular wire. This cumulated image represents a single phase ('freeze' time point) within the cardiac cycle, and as such cardiac motion is eliminated. This is further illustrated by reference to FIG. 20. Within FIG. 20, 2001 represents the x-ray fluoroscopic image sequence, in which each dot represents a successive x-ray fluoroscopic image frame within the x-ray fluoroscopic image sequence. Within step 1901, the radiopaque wire section as visible in the x-ray fluoroscopic image frames is detected at least in all frames which has the same phase within a cardiac cycle as determined by step 102 of FIG. 1. Within FIG. 20, as an example, this phase is selected as the R-top (2005) of the ECG signal (2002). Picture 2003 shows an x-ray fluoroscopic frame at R-top time moment 2009, and picture 2004 shows an x-ray fluoroscopic frame at the same cardiac phase (R-top) but that within a different cardiac cycle (2010). The detection of the radiopaque wire section (2006) is described by step 1901, and breathing motion, and possible patient motion has been corrected by detection of the catheter (tip) is described by step 1902. When performing this step for all frames which has the same phase within a cardiac cycle as determined by step by step 102 of FIG. 1, and in the example of FIG. 20 the phase selected is the R-top, a cumulated image (2008) is created. This image will contain no cardiac motion and no breathing and/or patient motion. Picture 2011 shows another example of such cumulated image, in this image only contains the segmented radiopaque wire section from all the frames at the selected phase, and may be smoothed to results in one single segmentation object. This cumulated image also directly contains the link of spatial location within the cumulated image to the intravascular image data, since in step 102 of FIG. 1, the synchronization is established between the x-ray fluoroscopic image data and the intravascular image data. This is illustrated in FIG. 20, by 2012 and 2011, in which 2012 represents the intravascular image data (in the example pressure values). On signal 2012, the values at the R-top (phase) are illustrated by V1 up to and including V5. These values can be directly linked to the cumulated image, as shown in picture 2011.

At step 1905, a superimposed cumulative image on x-ray angiographic is created. Within step 1904 an image is created providing information about the wire positions during the pullback of the intravascular wire. However, that image is created using an x-ray fluoroscopic image sequence (step 304 of FIG. 3) which is acquired without administration of a contrast agent and therefore lacking the ability to provide visual feedback to the user of any vessel structures. To provide this feedback, within step 1905 the cumulated image is superimposed onto an x-ray angiographic frame from the x-ray angiographic image data as a result from step 302 of FIG. 3. The x-ray angiographic frame is selected from the x-ray angiographic sequence as a frame at the same phase as used during the creation of the cumulated image (step 1901), similar to step 1001 or step 1002, and during the period after the contrast agent enters the coronary vessel of interest. The frame in which the contrast bolus arrives can be detected by analyzing the x-ray angiographic image data (302) as for instance taught by Ma et al., "*Fast prospective detection of contrast inflow in x-ray angiograms with convolutional neural network and recurrent neural network*", International Conference on Medical Image Computing and Computer-Assisted Intervention, Springer (2017) 453-461.

Figure 21:
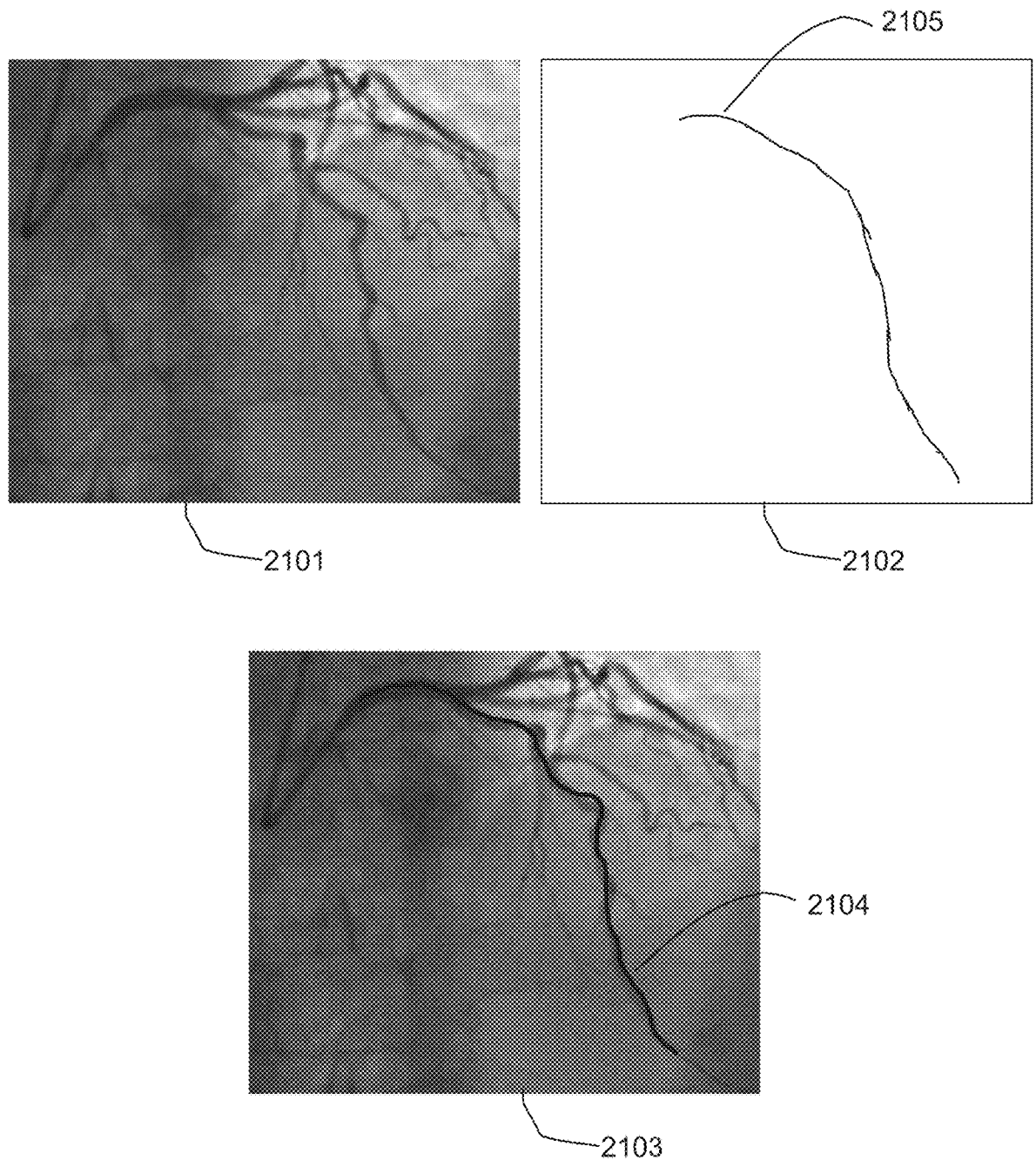
FIG. 21 shows an illustration of the creation of the superimposed cumulative image on an x-ray angiographic image frame.

After the correct x-ray angiographic image frame is selected, the cumulated image is superimposed onto the selected x-ray angiographic frame as for example by using registration techniques. The cumulated image (2008 or 2011) represents the segmented radiopaque wire section of each selected phase within the successive cardiac cycles and represents the pullback of the intravascular wire. Since the intravascular wire is located inside the vessel, the cumulative image (2008 or 2011) must be inside the vessel and hence can be used for image registration as the vessel location. Note that when using an image frame of the same cardiac phase as chosen to detect the wire positions in step 1901, the registration becomes easier since cardiac motion is already reduced. The registration can be performed using several techniques. One can align labeled features by first segmenting the vessel in x-ray angiographic image frame. The centerline of the segmentation can then be positioned on top of the wire positions. Alternatively image registration can be used. For example, one can create an "artificial" vessel around the wire position trajectory end register this artificial vessel image onto the contrast image 302 (FIG. 3) using for example non-rigid B-spline image registration techniques minimizing the Mean squared difference between the two images (Klein et al., "*Elastix: a toolbox for intensity-based medical image registration*", Med. Imag. IEEE Trans. 29 (1), 196-205) or other image (non)rigid registration techniques. FIG. 21 provides an illustration of the creation of the superimposed cumulative image on an x-ray angiographic image frame. Within FIG. 21, 2101 represent an x-ray angiographic image frame in which the coronary vessel were the intravascular wire is pull backed is visible. This frame is from the x-ray angiographic image data as a result of step from step 302 of FIG. 3 and is preferably a phase as used to create the detect the radiopaque wire section (step 1901). Picture 2102 shows the cumulated image as a result of step 1904, and 2103 shows the superimposed cumulative image on the x-ray angiographic image frame. Note that the segmented radiopaque wire sections (2105) is deformed (2104) as a result of the image registration as described above in image 2103.

Step 104: Display Data and Perform Advance Analysis

Figure 22A:
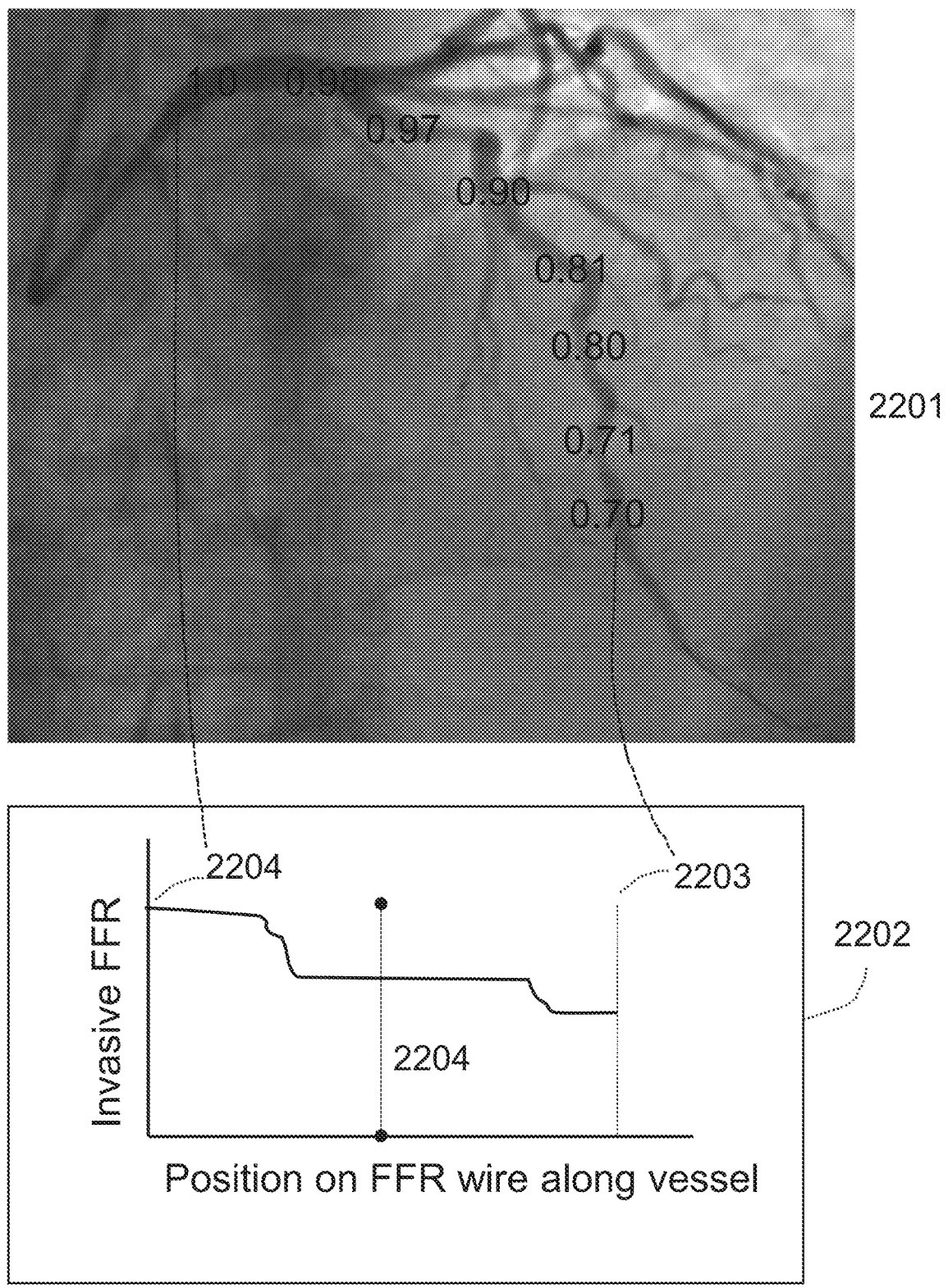
FIG. 22A shows an example of providing the result of the co-registration in which the intravascular imaging modality represents an FFR modality (1D intravascular image data).

At step 104, the result of the co-registration of an intravascular modality (intra-object) with x-ray angiographic imaging modality (inter-object) are provided. One example of providing the result of the co-registration is illustrated by FIG. 22A, in which the intravascular modality represents a FFR modality (1D intravascular image data). Within FIG. 22A, 2201 represents the x-ray angiographic image data as a result of step from step 302 of FIG. 3 and is preferably a frame representing the phase as used to create the detect the radiopaque wire section (step 1901). Picture 2202 provides the pressure curve as a result of the pullback as described by step 304 of FIG. 3. Within 2202, 2203 represent the most distal position of the intravascular wire and may represent the pressure value corresponding to the start of pullback as a result of step 1903 of FIG. 19. Within 2202, 2204 represents the most proximal position of the intravascular wire. Optionally this position may also be automatically defined, similar to the technique as described by step 1903, but now this position is defined in which the movement curve does not change in length (predefined threshold) within a predefined time. Within picture 2201, the co-registered pressure values may be superimposed on predefined intervals along the 'Position on FFR wire along vessel' axis (2202). This results in superimposing of for instance 0.70 (2201) which corresponds to position 2203 and superimposing of 1.0 (2201) which corresponds to position 2204. Alternatively, the co-registered values (pressure) are highlighted when the user hovers with the mouse over the curve (2202) or drags the marker 2204 along the curve.

Figure 22B:
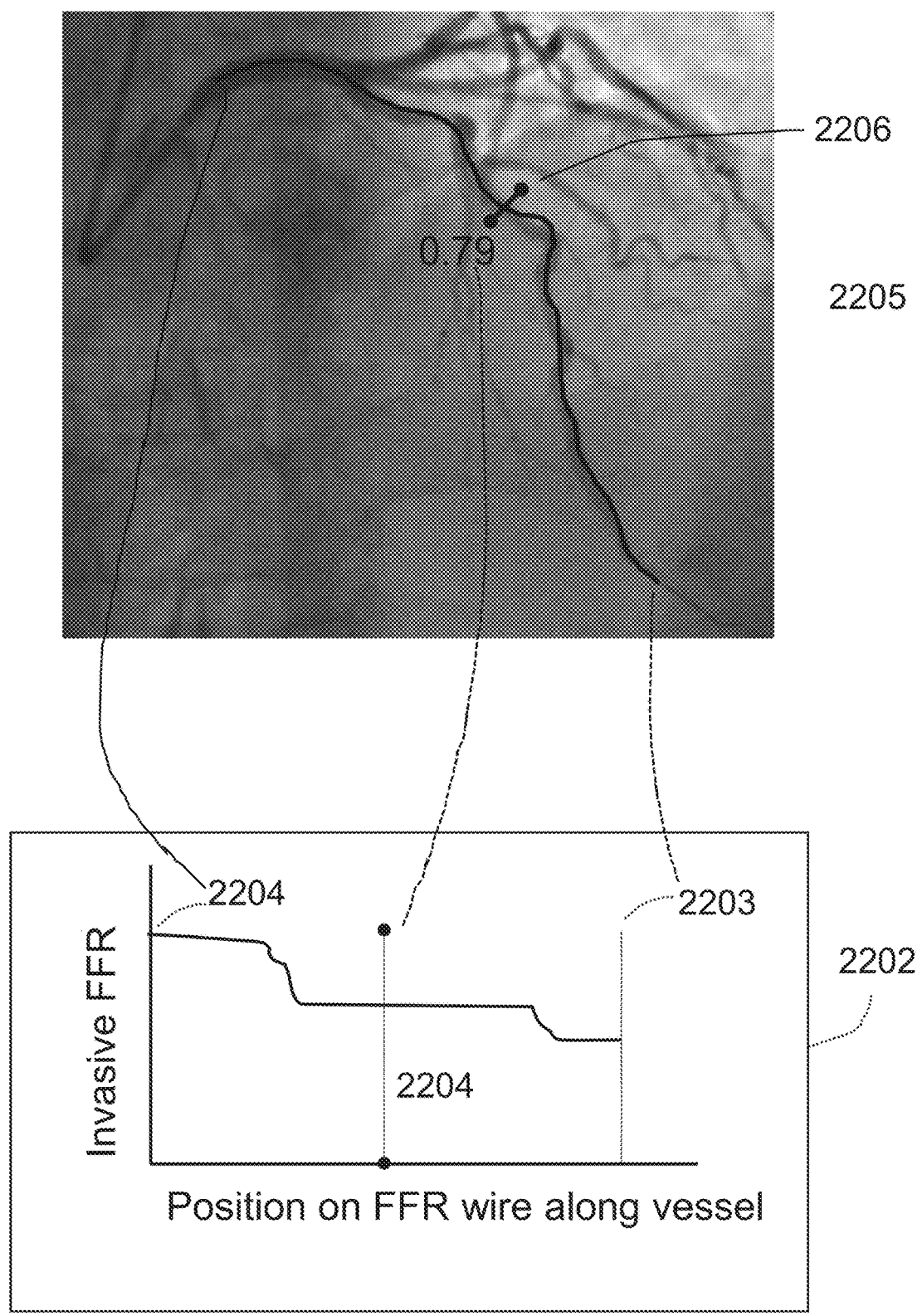
FIG. 22B shows another example of providing the result of the co-registration in which the intravascular imaging modality represents an FFR modality (1D intravascular image data).

FIG. 22B illustrated another example of providing the co-registration results and also in this example the intravascular imaging modality represents a FFR, iFR or modality. This visualization is similar as provided in FIG. 22A, although in FIG. 22B the x-ray angiographic frame also visualized the segmented radiopaque wire sections as a result of step 1905. The user is allowed to hover with the mouse over the curve (2202), or drags the marker 2204 along the curve, which results that the marker (2204), is visualized in 2205 along with its corresponding pressure value (2206).

Figure 23:
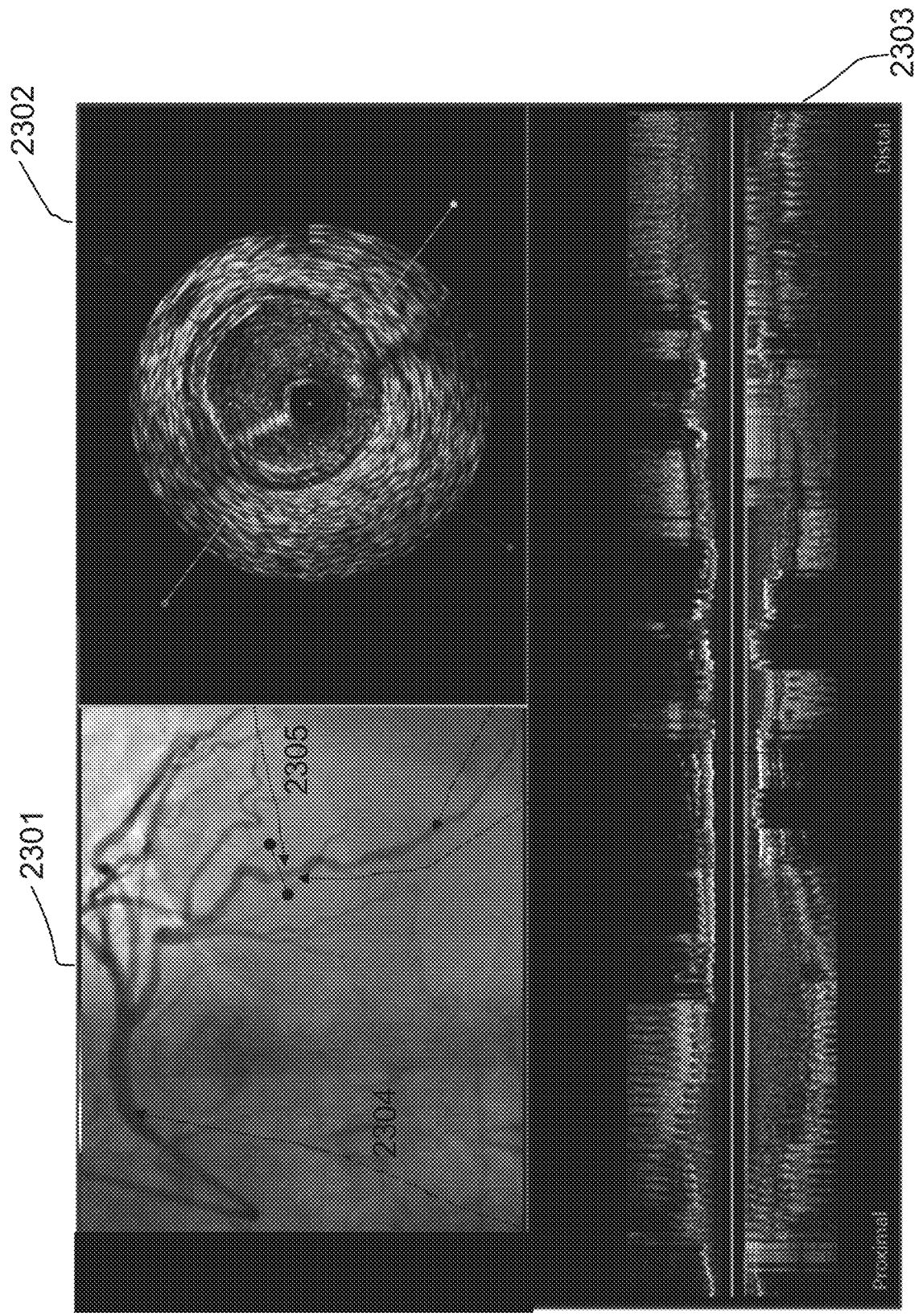
FIG. 23 shows an example of providing the result of the co-registration in which the intravascular imaging modality represents an IVUS modality (2D intravascular image data).

FIG. 23 illustrated an example of providing the result of the co-registration in which the intravascular imaging modality represents an IVUS modality (2D intravascular image data). Within FIG. 23, 2301 represents the x-ray angiographic image data as a result of step from step 302 of FIG. 3 and is preferably a frame representing the phase as used to create the detect the radiopaque wire section (step 1901). Picture 2303 represents a longitudinal view of the IVUS image data. A longitudinal view is an image wherein the intravascular frames acquired during pull back are stacked on each other along a longitudinal line (e.g. 2307). Picture 2302 provides an illustration of a single cross section IVUS frame. As a result of the co-registration in accordance with the patient application, position 2306 corresponds to the most distal position of the intravascular wire, and position 2304 corresponds to the most proximal position of the intravascular wire. At location 2305, the corresponding IVUS frame is visualized by 2302. The user is allowed to hover with the mouse over the longitudinal view (2303), or drags the marker 2305 along the curve, which results that the marker (2305), is visualized in 2301 along with it corresponding IVUS frame (2302).

Figure 24:
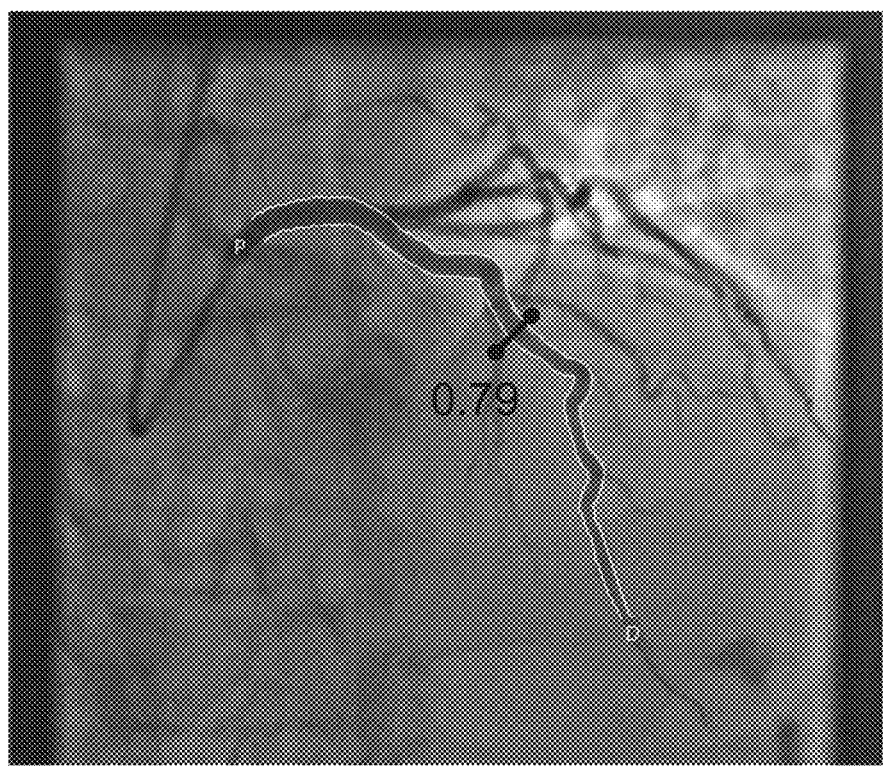
FIG. 24 shows an example of combining geometric information of the vessel of interest with the co-registration.
Figure 24:
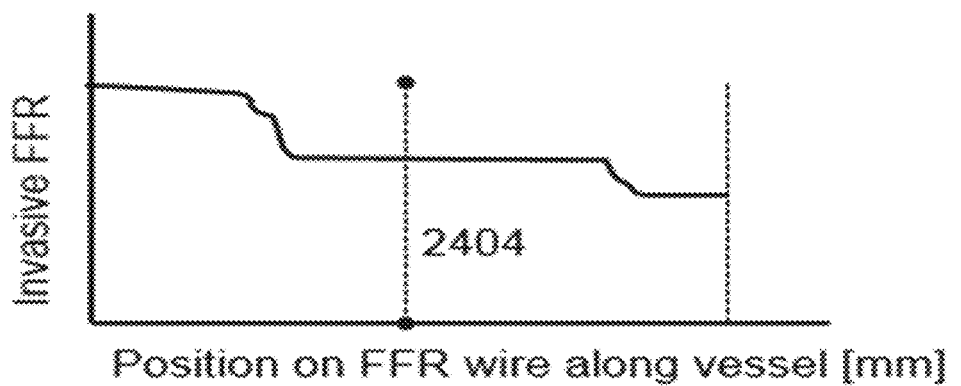
Figure 24:
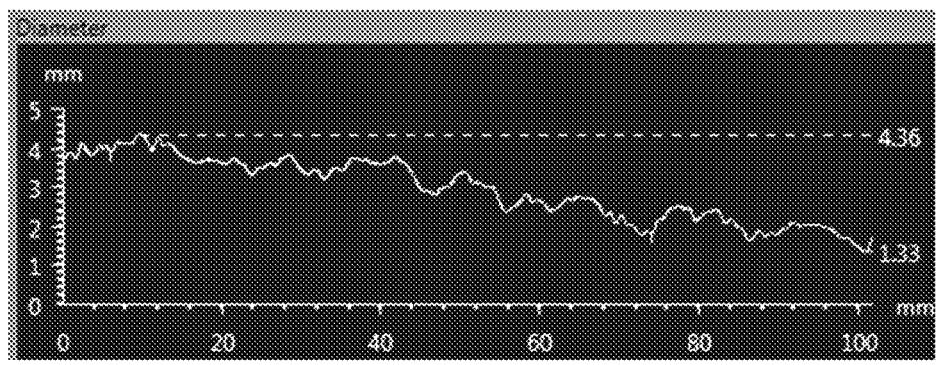

Alternatively, the path of the intravascular wire may be automatically segmented as for instance taught by Gronenschild E, et al. in "*CAAS II: A Second Generation system for Off-Line and On-Line Quantitative Coronary Angiography*", Cardiovascular Diagnosis 1994; 33: 61-75. This will allow visualization of geometrical information along with the co-registration. The segmentation may be initiated by the segmented radiopaque wire sections as a result of step 1905, or the user identifies the vessel of interest. The segmentation is performed in the x-ray angiographic image data as a result of step from step 302 of FIG. 3 and is preferably a frame representing the phase as used to create the detect the radiopaque wire section (step 1901). FIG. 24 provides an example of combining geometric information of the vessel of interest with the co-registration. The intravascular imaging modality within the example in FIG. 24 represents a FFR modality (1D intravascular image data) as shown by 2402. The segmentation is visualized on the x-ray angiographic frame (2401) and geometrical results are extracted as for example diameter along the vessel (2403). The user is allowed to hover with the mouse over the curve (2404), or drags the marker 2404 along the curve, which results that the marker (2404), is visualized in 2401 along with its corresponding pressure value. Please note that the x-axis of the pressure curve (2402) and diameter curve (2403) is represented in millimeter. This can be accomplished by performing a calibration on the x-ray angiographic image frame. Such a calibration translates a pixel into physical dimension, in the example millimeter, and can be performed for instance by using the geometrical information of the x-ray system in which the x-ray angiographic image was acquired (distance x-ray source to image intensifier, distance x-ray source to object and pixel size at the image intensifier), or other techniques as know by prior art. Alternatively, the calibration (determination of the pixel size) can be performed by the method described by the following section "Pixel size and foreshortening determination".

Pixel Size and Foreshortening Determination

The intravascular wire contains a sensor (402, FIG. 4A, FIG. 4B) which performs the imaging, and a radiopaque wire section (403, FIG. 4A, FIG. 4B). The length of this radiopaque wire section is specified by the manufacturer which delivers the intravascular wire. This radiopaque wire section is visible within the x-ray fluoroscopy image sequence.

For the estimation of the pixel size and foreshortening factor, the assumption can be made that the x-ray fluoroscopic image frame within the x-ray fluoroscopic sequence, at the time (frame) that the radiopaque wire section has the longest distance, is the frame where no foreshortening is available. By this assumption, the pixel size can be estimated by use of the length in pixels of the detected radiopaque wire section (step 1901) within this image frame (without foreshortening) and the specified length of the intravascular device radiopaque wire section.

Figure 25:
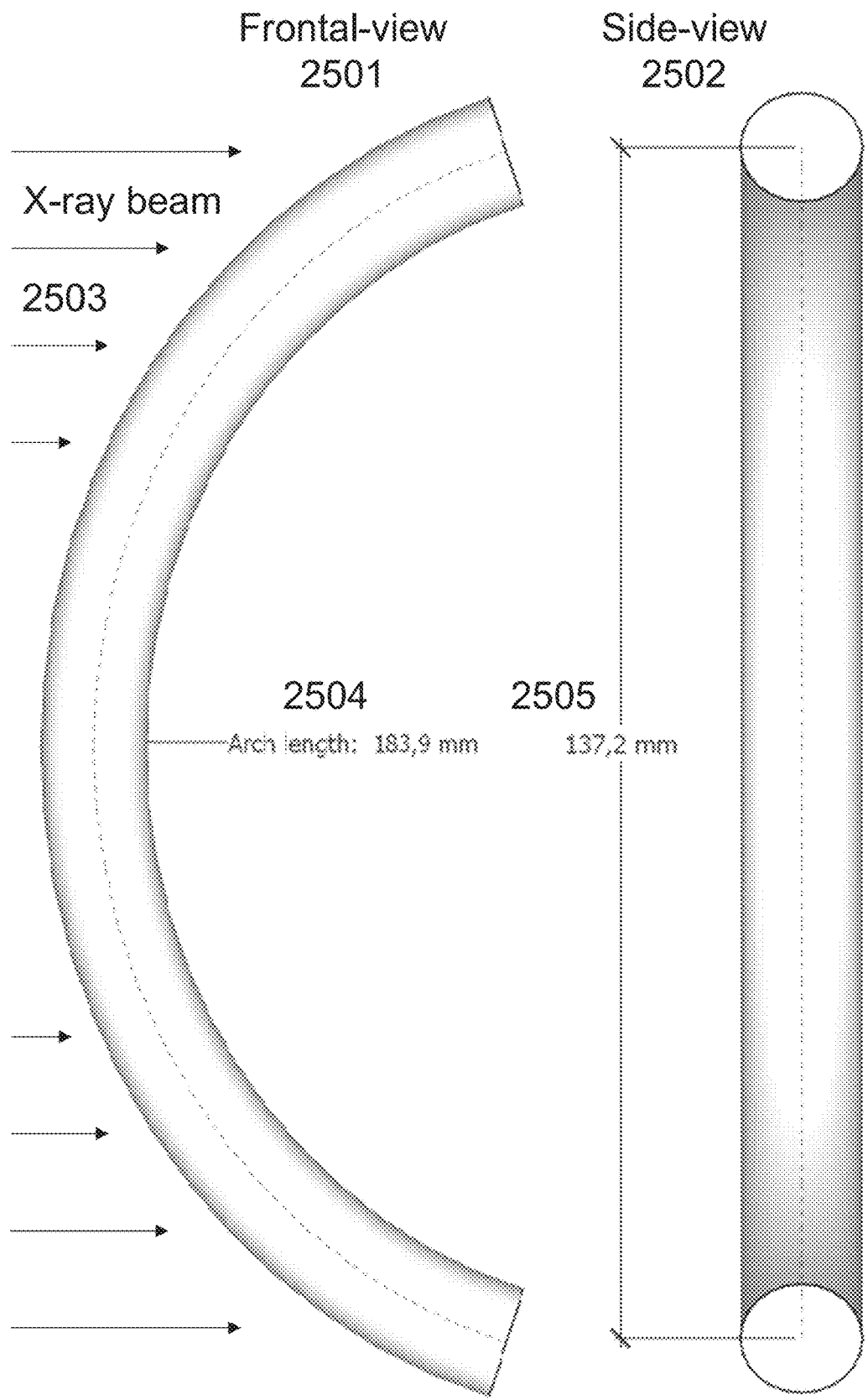
FIG. 25 shows an illustration of foreshortening.

Moreover, the amount of foreshortening present in the x-ray image data can be expressed along pullback path. Since x-ray angiography is a 2D imaging modality that visualized a 3D structure into a 2D image "foreshortening" can occur. Foreshortening is the event when an object (e.g. vessel) seems compressed (e.g. the length of the vessel is visualized in 2D shorter) when viewed from a certain perspective and foreshortening refers to images of vascularity and other structures in the x-ray appear too short. This is due to an excessive vertical angulation of the x-ray tube whilst taking the radiograph. An example of this is visualized within FIG. 25. Within Frontal-view (2501) of FIG. 25, the vessel (2504) is shown without foreshortening. The side-view (2502) is the x-ray view which is acquired based on the x-ray beam 2503. This view contains foreshortening which is variable along the length of the vessel and result in an x-ray image 2505.

Figure 26:
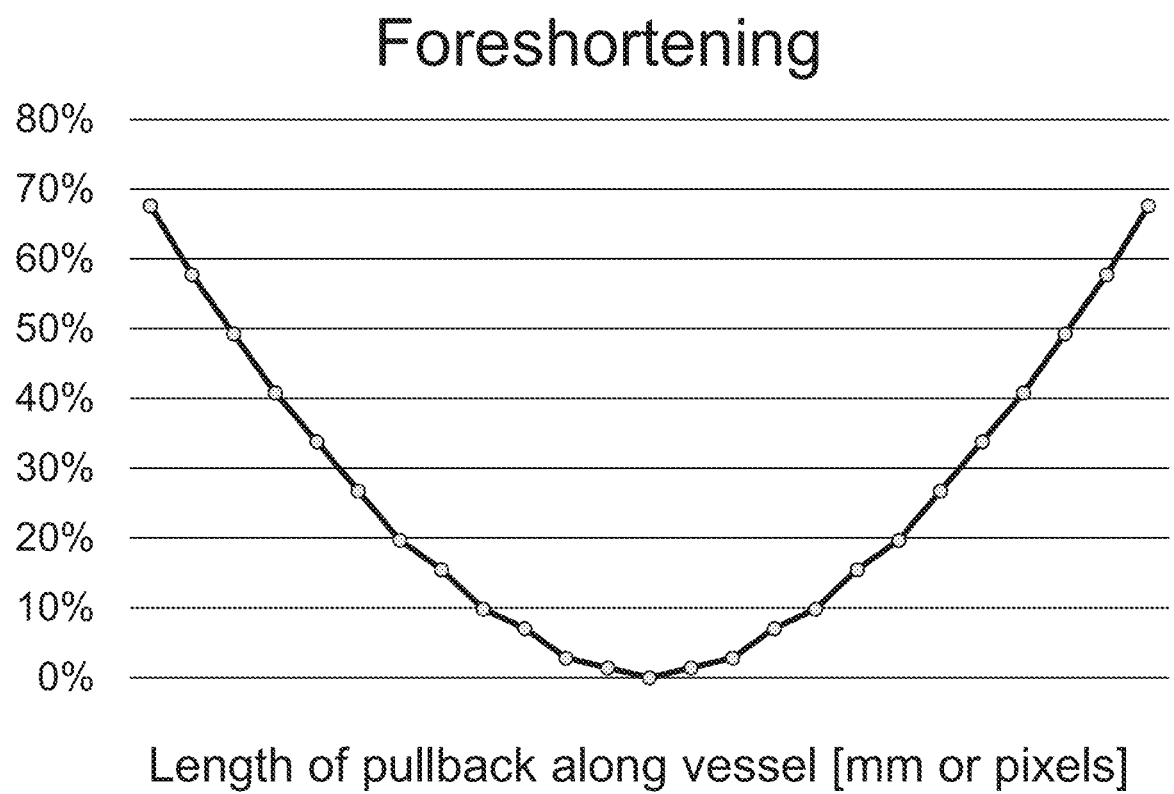
FIG. 26 shows an example of presenting the amount of foreshortening along the length of the pullback.

During pullback of the FFR wire, successive image frames are available wherein the radiopaque wire section is visible which can be detected automatically (see step 1901). The x-ray image frame(s) where the length of the sensor part has the maximum values, can be used as reference for the image frames where the length of the sensor part is smaller. For each frame, the length of the sensor part is estimated from where the change in length against the reference length can be determined (foreshortening), which is shown in FIG. 26. The y-axis represents the foreshortening value and the x-axis represents the position along the length of the pullback, either in pixels or millimeter.

Focal/Diffuse

FFR measurements presented along the geometry of interest illustrated by FIG. 22A or FIG. 22B, possibly combined with geometric quantifications obtained from the geometry, can be used to provide added value in clinical decision making. The data can, for example, be used to determine if a lesion is focal or diffuse, providing information for the treatment plan. Focal lesions for example can be more easily treated by dilating the stenosis using an inflatable balloon possibly followed by stent or scaffold placement. Diffuse lesions are more difficult to treat and may need different treatment strategies like medication preventing unnecessary patient risk and costs. This decision making can be based on the shape of the FFR curve along the geometry possibly combined with geometric information like diameter/area changes and length. For example, a fast local decrease in FFR or pressure drop indicates a more local lesion.

System Configurations

The present application relates to a method and system for co-registration of an intravascular imaging modality (intra-object) with x-ray angiographic imaging modality (inter-object). This section provides several examples of system configurations in which the operations of the present application are utilized. FIG. 27 illustrates the different high level system components, and exists of an x-ray imaging system (2701), an intravascular imaging system (2702) and a system in which the operations of current application are executed for instance a computer system (2703). In general, the system in which the operations of current application are executed, block 2703, receives and process data received from the x-ray imaging system (2701) and the intravascular imaging system (2702). The data received from the x-ray imaging system consist of x-ray image data and possibly ECG data, and the data received from the intravascular imaging system consists of intravascular imaging data as for instance cross sectional images in case of IVUS, OCT intravascular imaging system or pressure image data in case of a FFR, iFR or CFR intravascular imaging system. Such data transfer from the x-ray imaging system (2701) and intravascular imaging system (2702) towards to the system in which the operations of current application are executed (2703) can be by means of file transfer, memory transfer, or by digitalizing the imaging data.

In the first exemplary system the method receives the x-ray image data using a frame grabber or a digital visual interface (DVI), and possibly collects the ECG signal using an analog to digital (A/D) converter. The data from the intravascular imaging system is received by either a frame grabber or a DVI in case of intravascular system like for instance IVUS or OCT, or by an A/D converter in case of a FFR, iFR or CFR intravascular imaging system.

In the second exemplary system the data transfer is arranged by file transfer as for instance by the DICOM file standard. In this situation the method can be performed on a standalone computer system being physically separated from the imaging devices. Because the data is stored in files no direct connection between the x-ray and intravascular imaging systems is needed and the method can be used offline.

In both described system configurations, the operations according to embodiments herein can be integrated on the x-ray imaging system or on the intravascular imaging system or on a separate computer system.

In case the operations of the present application are part of the x-ray imaging system, the x-ray image data and possible the ECG data is in a preferred embodiment transferred to the operations of current application by means of memory transfer. The data transfer between the x-ray imaging system and the intravascular imaging system with respect to the data required by current application is in a preferred embodiment transferred by means of a frame grabber or a DVI in case of intravascular system like for instance IVUS or OCT, or by means of an A/D converter in case of a FFR, iFR or CFR intravascular imaging system.

In case the operations of the present application are part of the intravascular imaging system, the intravascular data is in a preferred embodiment transferred to the operations of current application by means of memory transfer. The data transfer between the intravascular imaging system and the x-ray imaging system with respect to the data required by current application is in a preferred embodiment transferred by means of a frame grabber or a digital visual interface (DVI), and possibly collects the ECG signal using an analog to digital (A/D) converter.

Figure 17:
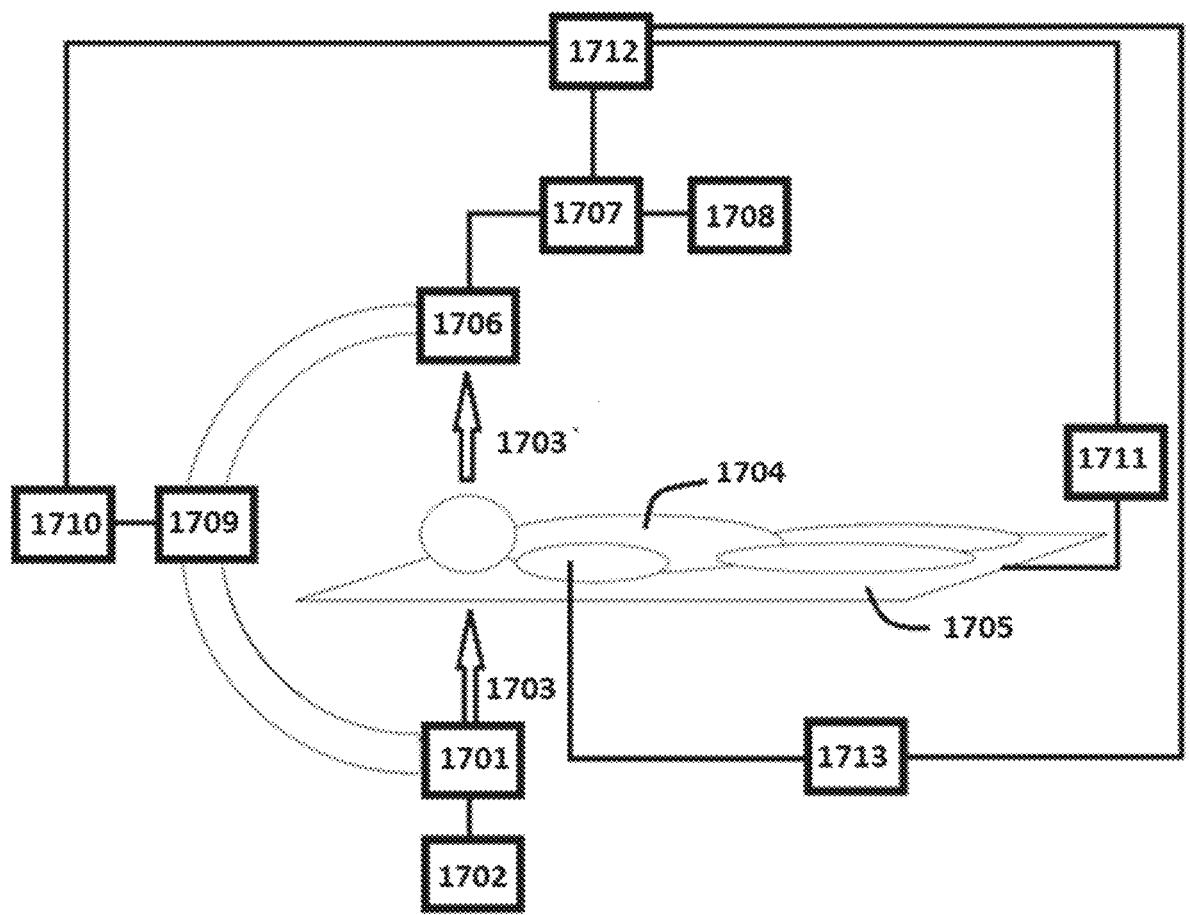
FIG. 17 shows an example of an x-ray cinefluorographic unit block diagram in accordance with embodiments herein.

Operations can be performed by processor unit on a standalone system, or a semi-standalone system which is connected to the x-ray system (FIG. 2) and described in more detail with reference to FIG. 27, or included directly in, for instance, an x-ray fluorography system or any other image system to acquire two dimensional angiographic image sequences (FIG. 2). FIG. 17 illustrates an example of a high-level block diagram of an x-ray cinefluorograpic system. In this block diagram an example is shown on how embodiments could integrate in such a system.

Portions of the system (as defined by various functional blocks) may be implemented with dedicated hardware, analog and/or digital circuitry, and/or one or more processors operating program instructions stored in memory.

The x-ray system of FIG. 17 includes an x-ray tubes 1701 with a high voltage generator 1702 that generates an x-ray beam 1703. The high voltage generator 1702 controls and delivers power to the x-ray tube 1701. The high voltage generator 1702 applies a high voltage across the vacuum gap between the cathode and the rotating anode of the x-ray tube 1701. Due to the voltage applied to the x-ray tube 1701, electron transfer occurs from the cathode to the anode of the x-ray tube 1701 resulting in x-ray photon-generating effect also called Bremsstrahlung. The generated photons form an x-ray beam 1703 directed to the image detector 1706.

An x-ray beam 1703 comprises of photons with a spectrum of energies that range up to a maximum determined by among others the voltage and current submitted to the x-ray tube 1701. The x-ray beam 1703 then passes through the patient 1704 that lies on an adjustable table 1705. The x-ray photons of the x-ray beam 1703 penetrate the tissue of the patient to a varying degree. Different structures in the patient 1704 absorb different fractions of the radiation, modulating the beam intensity. The modulated x-ray beam 1703' that exits from the patient 1704 is detected by the image detector 1706 that is located opposite of the x-ray tube. This image detector 1706 can either be an indirect or a direct detection system.

In case of an indirect detection system, the image detector 1706 comprises of a vacuum tube (the x-ray image intensifier) that converts the x-ray exit beam 1703' into an amplified visible light image. This amplified visible light image is then transmitted to a visible light image receptor such as a digital video camera for image display and recording. This results in a digital image signal.

In case of a direct detection system, the image detector 1706 comprises of a flat panel detector. The flat panel detector directly converts the x-ray exit beam 1703' into a digital image signal. The digital image signal resulting from the image detector 1706 is passed through a digital image processing unit 1707. The digital image processing unit 1707 converts the digital image signal from 1706 into a corrected x-ray image (for instance inverted and/or contrast enhanced) in a standard image file format for instance DICOM. The corrected x-ray image can then be stored on a hard drive 1708.

Furthermore, the x-ray system of FIG. 17 comprises of a C-arm 1709. The C-arm holds the x-ray tube 1701 and the image detector 1706 in such a manner that the patient 1704 and the adjustable table 1705 lie between the x-ray tube 1701 and the image detector 1706. The C-arm can be moved (rotated and angulated) to a desired position to acquire a certain projection in a controlled manner using the C-arm control 1710. The C-arm control allows for manual or automatic input for adjustment of the C-arm in the desired position for the x-ray recording at a certain projection.

The x-ray system of FIG. 17 can either be a single plane or a bi-plane imaging system. In case of a bi-plane imaging system, multiple C-arms 1709 are present each consisting of an x-ray tube 1701, an image detector 1706 and a C-arm control 1710.

Additionally, the adjustable table 1705 can be moved using the table control 1711. The adjustable table 1705 can be moved along the x, y and z axis as well as tilted around a certain point.

Furthermore, a measuring unit 1713 is present in the x-ray system. This measuring unit contains information regarding the patient, for instance information regarding ECG, aortic pressure, biomarkers, and/or height, length etc.

A general unit 1712 is also present in the x-ray system. This general unit 1712 can be used to interact with the C-arm control 1710, the table control 1711, the digital image processing unit 1707, and the measuring unit 1713.

An embodiment is implemented by the x-ray system of FIG. 17 as follows. A clinician or other user acquires at least two x-ray angiographic image sequences of a patient 1704 by using the C-arm control 1710 to move the C-arm 1709 to a desired position relative to the patient 1704. The patient 1704 lies on the adjustable table 1705 that has been moved by the user to a certain position using the table control 1711.

The x-ray image sequences are then generated using the high voltage generator 1702, the x-ray tube 1701, the image detector 1706 and the digital image processing unit 1707 as described above. These images are then stored on the hard drive 1708. Using these x-ray image sequences, the general processing unit 1712 performs the methods as described by present application, as for instance as described by FIG. 1 using the information of the measuring unit 1713, the digital image processing unit 1707, C-arm control unit 1710 and the table control unit 1711.

There have been described and illustrated herein several embodiments of a method and apparatus for restoring missing information regarding the order and the flow direction of the velocity components. While particular embodiments of the invention have been described, it is not intended that the invention be limited thereto, as it is intended that the invention be as broad in scope as the art will allow and that the specification be read likewise. For example, the data processing operations can be performed offline on images stored in digital storage, such as a PACS commonly used in the medical imaging arts. It will therefore be appreciated by those skilled in the art that yet other modifications could be made to the provided invention without deviating from its spirit and scope as claimed.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer, or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. A method for correlating intraluminal data with x-ray image data, comprising:
providing x-ray image data of a tubular organ;
providing intraluminal data of the tubular organ;
synchronizing the x-ray image data with the intraluminal data based on a cardiac cycle extracted from an available input signal and/or the x-ray image data and/or the intraluminal data to match x-ray image data with intraluminal data in a specific cardiac phase; and
co-registering x-ray image data with intraluminal data by creating a cumulative image at the specific cardiac phase which reconstructs a path followed by an intraluminal wire used for acquiring the intraluminal data to link the intraluminal data to spatial locations of the path followed by the intraluminal wire within the x-ray image;
wherein the coregistering involves determining a start of pullback of the intraluminal wire by analyzing a movement curve created by computing absolute distance of the intraluminal wire between a reference image frame and remaining image frames of the x-ray image data.

2. A method according to claim 1, wherein:
the cumulative image is created by extracting image frames from the x-ray image data containing the intraluminal wire at the same specific cardiac phase and forming an image of the intraluminal wire by cumulating the image frames as extracted.

3. A method according to claim 2, wherein:
before forming the cumulative image, the intraluminal wire is identified or segmented in the image frames.

4. A method according to claim 1, wherein:
the x-ray image data comprise fluoroscopic image data obtained without contrast agent and angiography image data obtained with contrast agent, the cumulative image being created from the fluoroscopic image data.

5. A method according to claim 4, further comprising:
superimposing the cumulative image on angiography image data.

6. A method according to claim 4, wherein:
the intraluminal data comprises numeric values, such numeric values being superimposed on the angiography image data at corresponding spatial locations.

7. A method according to claim 4, wherein:
the intraluminal data comprises intraluminal images, the method further comprises receiving an input to select a spatial location within the angiography image data and showing intraluminal images which has been taken from such spatial location.

8. A method according to claim 1, further comprising:
correcting breathing and/or patient motion by tracking a catheter tip within the x-ray fluoroscopic image data.

9. A method according to claim 1, wherein:
the x-ray image data and the intraluminal data have a known temporal relation, wherein synchronizing the x-ray image data with the intraluminal data comprises extracting a cardiac cycle from an ECG signal, the x-ray image data or the intraluminal data, selecting a specific cardiac phase, calculating delays between the specific cardiac phase and the x-ray image data and the intraluminal data, aligning the x-ray image data and the intraluminal data by correcting the delays as calculated.

10. A method according to claim 1, further comprising:
extracting cardiac cycles from the x-ray image data, or from an ECG signal correlated with the x-ray image data;
from the intraluminal data, identifying a specific cardiac phase in the cardiac cycles as extracted;
calculating delays between the specific cardiac phase in the x-ray image data and the intraluminal data; and
aligning the x-ray image data and the intraluminal data by correcting the delays as calculated.

11. A method according to claim 1, wherein:
a reliability of an ECG signal is assessed by aligning the ECG signal with a template and determining a correlation function between the ECG signal and such template.

12. A method according to claim 1, wherein:
the x-ray image data comprise image frames including a fixed element subject to cardiac motion, and the method further comprises determining cardiac motion of the fixed element, and extracting from such cardiac motion a cardiac cycle.

13. A method according to claim 12, wherein:
the cardiac motion of the fixed element is determined by enhancing structures subject to the cardiac motion in the image frames.

14. A method according to claim 13, further comprising:
using principal component analysis to enhance the structures subject to cardiac motion in the image frames.

15. A method according to claim 12, wherein:
the fixed element comprises a catheter tip.

16. A method according to claim 12, wherein:
the cardiac motion of the fixed element is determined through image segmentation or machine learning.

17. A method according to claim 1, wherein:
the intraluminal data comprises bi-dimensional images, and the method further comprises determining motion of a lumen border with respect to a reference point or line, and extracting from such motion a cardiac cycle.

18. A method according to claim 17, wherein:
the motion of the lumen border is determined by calculating the distance from the reference point or line to the lumen border in each or part of the bi-dimensional images and combining the distances as calculated to reconstruct the cardiac cycle.

19. A method according to claim 17, wherein:
the reference point or line comprises a location of an imaging probe used for acquiring the images.

20. A method according to claim 1, wherein:
the intraluminal data comprises non-imaging data, and the method further comprises determining periodic features in the non-imaging data and extracting from such periodic features a cardiac cycle.

21. A system for registering x-ray images with intraluminal data of a tubular organ comprising:
an angiographic imaging apparatus for obtaining x-ray images of the tubular organ;
an intravascular apparatus for obtaining intraluminal data of the tubular organ; and a combination device comprising a data processing module, and interface elements for receiving x-ray images from the angiographic imaging apparatus and intraluminal data from the intravascular apparatus, wherein the data processing module is configured to synchronize the x-ray image data with the intraluminal data based on a cardiac cycle extracted from an available input signal and/or the x-ray image data and/or the intraluminal data to match x-ray image data with intraluminal data in a specific cardiac phase and co-register the x-ray image data with intraluminal data by creating a cumulative image at the specific cardiac phase which reconstructs a path followed by an intraluminal wire used for acquiring the intraluminal data to link the intraluminal data to spatial locations of the path followed by the intraluminal wire within the x-ray image, wherein the co-registration of the x-ray image data with the intraluminal data involves determining a start of pullback of the intraluminal wire by analyzing a movement curve created by computing absolute distance of the intraluminal wire between a reference image frame and remaining image frames of the x-ray image data.

22. A system according to claim 21, wherein:

the combination device is part of the angiography imaging apparatus;

the data processing module of the combination device comprises one of the processors of the angiographic imaging apparatus having access to the x-ray images; and the angiographic imaging apparatus has an input for receiving intraluminal data from the intravascular apparatus.

23. A system according to claim 21, wherein:

the combination device is part of the intravascular apparatus;

the data processing module of the combination device comprises a processor of the intravascular apparatus having access to the intraluminal data; and the intravascular apparatus has an input for receiving x-ray images from the x-ray imaging apparatus.

24. A system according to claim 21, further comprising:

an ECG module interfaced with the x-ray apparatus, the intravascular apparatus or the combination device configured to allow the data processing module to elaborate an ECG signal.

25. A system according to claim 21, wherein:

the x-ray images, the intravascular data, and the ECG signal are input to the combination device, at least in part, through a frame grabber, an A/D converter, a DICOM transfer protocol or combination thereof.

26. A system according to claim 21, wherein:

the intravascular apparatus comprises an intraluminal wire having a sensor for collecting intraluminal data through a console while the intraluminal wire is pulled through the tubular organ, such sensor being suitable for collecting intraluminal data selected from a group consisting of: FFR, iFR, CFR, IVUS, OCT data.

* * * * *